United States Patent
Ohmori et al.

(10) Patent No.: US 11,970,706 B2
(45) Date of Patent: Apr. 30, 2024

(54) GENETICALLY MODIFIED RAT THAT EXPRESSES AN F54L Txn1 MUTANT

(71) Applicants: Iori Ohmori, Okayama (JP); Mamoru Ouchida, Okayama (JP); Tomoji Mashimo, Tokyo (JP); HAMAMATSU PHOTONICS K.K., Hamamatsu (JP)

(72) Inventors: Iori Ohmori, Okayama (JP); Mamoru Ouchida, Okayama (JP); Tomoji Mashimo, Tokyo (JP)

(73) Assignees: Iori Ohmori, Oukayama (JP); Mamoru Ouchida, Oukayama (JP); Tomoji Mashimo, Tokyo (JP); HAMAMATSU PHOTONICS K.K., Hamamatsu (JP)

( * ) Notice: Subject to any disclaimer, the term of this patent is extended or adjusted under 35 U.S.C. 154(b) by 473 days.

(21) Appl. No.: 16/771,541

(22) PCT Filed: Dec. 6, 2018

(86) PCT No.: PCT/JP2018/045008
§ 371 (c)(1),
(2) Date: Jun. 10, 2020

(87) PCT Pub. No.: WO2019/117022
PCT Pub. Date: Jun. 20, 2019

(65) Prior Publication Data
US 2021/0171978 A1    Jun. 10, 2021

(30) Foreign Application Priority Data
Dec. 13, 2017 (JP) .................. 2017-238612

(51) Int. Cl.
*A01K 67/027* (2006.01)
*C12N 15/85* (2006.01)
(52) U.S. Cl.
CPC .. *C12N 15/8509* (2013.01); *C12N 2015/8527* (2013.01)
(58) Field of Classification Search
None
See application file for complete search history.

(56) References Cited

U.S. PATENT DOCUMENTS

| | | |
|---|---|---|
| 2003/0223980 A1 | 12/2003 | Powis |
| 2005/0257279 A1 | 11/2005 | Qian et al. |
| 2017/0136100 A1* | 5/2017 | Das .................. A61K 38/44 |

OTHER PUBLICATIONS

Booze (Free Radical Biol. And Med., 2016, vol. 99, p. 533-543).*
Yamamoto (J. Clin. Invest., 2003, vol. 112, p. 1395-1406).*
MGI mammalian phenotype browser description of Renal morphology dysfunction, 2023.*
MGI mammalian phenotype browser description of Renal physiology dysfunction, 2023.*
MGI mammalian phenotype browser description of increased brain cholesterol, 2023.*
MGI mammalian phenotype browser description of increased circulating HDL cholesterol, 2023.*
MGI mammalian phenotype browser description of increased circulating LDL cholesterol, 2023.*
MGI mammalian phenotype browser description of increased circulating VLDL cholesterol, 2023.*
MGI mammalian phenotype browser description of increased circulating cholesterol, 2023.*
MGI mammalian phenotype browser description of increased liver cholesterol, 2023.*
Perez Virginia et al., "Inhibition of endogenous thioredoxin-1 in the heart of transgenic mice does not confer cardioprotection in ischemic postconditioning", Corina Borghouts,Christian Q Scheckhuber,Oliver Stephan,Heinz D Osiewacz, Pergamon,GB, vol. 81,Sep. 25, 2016, p. 315-p. 322, XP029836849.
Booze, Michelle L., et al., "A Novel Mouse Model for the Identification of Thioredoxin-1 Protein Interactions," Free Radic Biol Med, 2016, vol. 99, p. 533-p. 543.
Gallegos, Alfred, et al., "Transfection with Human Thioredoxin Increases Cell Proliferation and a Dominant-negative Mutant Thioredoxin Reverses the Transformed Phenotype of Human Breast Cancer Cells," Cancer Res., 1996, vol. 56, p. 5765-p. 5770.
Hamada, Yasuhiro et al., "Overexpression of thioredoxin1 in Transgenic Mice Suppresses Development of Diabetic Nephropathy," Nephrol Dial Transplant, Jun. 2007 (vol. 22), p. 1547- p. 1557.
Matsui, Minoru et al., "Early Embryonic Lethality Caused by Targeted Disruption of the Mouse Thioredoxin Gene," Developmental Biology, Aug. 1996 (vol. 178), p. 179-p. 185.
Nakamura, Hajime et al., "Redox Regulation of Cellular Activation," Annual Review of Immunology , Apr. 1997 (vol. 15), p. 351-p. 369.
Oomori, Iori et al., "Multiple organ failure due to new Txn1 gene missense mutation", Programs and Abstracts of Annual meeting of Society for Free Radical Research Japan, Apr. 19, 2018,vol. 71st, p. 136, including partial English translation.
Perez, Viviana et al., "Thioredoxin 1 Overexpression Extends Mainly the Earlier Part of Life Span in Mice," The Journals of Gerontology: Series A, Dec. 2011 (vol. 66A), p. 1286-p. 1299.

(Continued)

*Primary Examiner* — Michael C Wilson
(74) *Attorney, Agent, or Firm* — Faegre Drinker Biddle & Reath LLP

(57) ABSTRACT

Provided is a nonhuman animal model that is obtained by modifying a gene encoding thioredoxin and useful as a disease model of aging, kidney diseases, cardiovascular diseases, hypertension, aortic dissection, chronic obstructive lung disease, age-dependent epilepsy, abnormality of lipid metabolism, anemia, osteoporosis, abnormal immunity, etc. These variety of phenotypes are caused by the fact that a modification of a gene encoding thioredoxin induces hypofunction of thioredoxin expressed in multiple organs throughout the body. The gene encoding thioredoxin is a gene selected from among TXN, TRX, TRX1, RRDX, Txn1, Txn, Trx1 and ADF.

5 Claims, 18 Drawing Sheets
Specification includes a Sequence Listing.

(56) References Cited

OTHER PUBLICATIONS

Powis, Garth et al., "Properties and Biological Activities of Thioredoxins," Annual Review of Biophysics and Biomolecular Structure, Jun. 2001 (vol. 30), p. 421-p. 455.

Yamamoto, Mitsutaka et al., "Inhibition of endogenous thioredoxin in the heart increases oxidative stress and cardiac hypertrophy", J. Clin. Invest., 2003, vol. 112, No. 9, p. 1395-p. 1406.

International Preliminary Report on Patentability mailed Jun. 25, 2020 for PCT/JP2018/045008.

Brian B. Ratliff et al, "Oxidant Mechanisms in Renal Injury and Disease", Antioxidants & Redox Signaling, vol. 25, No. 3, 2016, pp. 119-146.

Yachun Han et al., "Reactive oxygen species promote tubular injury in diabetic nephropathy: The role of the mitochondrial ros-txnip-nlrp3 biological axis", Redox Biology 16 (2018) pp. 32-46.

Kento Nishida et al., "Recombinant Long-Acting Thioredoxin Ameliorates AKI to CKD Transition via Modulating Renal Oxidative Stress and Inflammation", International Journal of Molecular Sciences, Int. J. Mol. Sci. 2021, 22, 5600, https://doi.org/10.3390/ijms22115600.

Alison Domingues et al., "The Emerging Role of TXNIP in Ischemic and Cardiovascular Diseases; A Novel Marker and Therapeutic Target", International Journal of Molecular Sciences, Int. J. Mol. Sci. 2021, 22, 1693, https://doi.org/10.3390/ijms22041693.

Hideyuki Yamawaki et al., "Thioredoxin A Key Regulator of Cardiovascular Homeostasis", Circulation Research, Nov. 28, 2003, pp. 1029-1033.

Haruka Tsubaki et al., "Thioredoxin-Interacting Protein (TXNIP) with Focus on Brain and Neurodegenerative Diseases", International Journal of Molecular Sciences, Int. J. Mol. Sci. 2020, 21, 9357; doi:10.3390/ijms21249357, pp. 1-24.

Julen Goikolea et al., "Serum Thioredoxin-80 is associated with age, ApoE4, and neuropathological biomarkers in Alzheimer's disease: a potential early sign of AD", Goikolea et al. Alzheimer's Research & Therapy, (2022) 14:37, pp. 1-13.

Naoya Tanabe et al., "Thioredoxin-1 Protects against Neutrophilic Inflammation and Emphysema Progression in a Mouse Model of Chronic Obstructive Pulmonary Disease Exacerbation", PLOS One, Nov. 2013, vol. 8, Issue 11, pp. 1-10.

Kazushi Matsumura et al., "Novel biomarker genes which distinguish between smokers and chronic obstructive pulmonary disease patients with machine learning approach", Matsumura and Ito BMC Pulmonary Medicine (2020) 20:29, pp. 1-13.

Eiji Yoshihara et al., "Thioredoxin/Txnip: redoxisome, as a redox switch for the pathogenesis of diseases", Frontiers in Immunology, Jan. 9, 2014, vol. 4, Article 514, pp. 1-9.

E.E. Groopman et al., "Diagnostic Utility of Exome Sequencing for Kidney Disease", The New England Journal of Medicine, 380;2, NEJM., Jan. 10, 2019, pp. 142-151.

António Nogueira et al., "Pathophysiological Mechanisms of Renal Fibrosis: A Review of Animal Models and Therapeutic Strategies", In Vivo 31: 1-22 (2017), pp. 1-22.

"Chapter 1: Definition and classification of CKD", Kidney International Supplements (2013) 3, pp. 19-62; http://www.kidney-international.org/.

Christine Wahlquist et al., "Inhibition of miR-25 Improves Cardiac Contractility in the Failing Heart", Nature, Apr. 24, 2014; 508(7497): 531-535, pp. 1-31.

Peter Lanzer et al., "Medial vascular calcification revisited: review and perspectives", European Heart Journal (2014) 35, pp. 1515-1525.

Bianca C. Bernardo et al., "Therapeutic inhibition of the miR-34 family attenuates pathological cardiac remodeling and improves heart function", PNAS, Oct. 23, 2012, vol. 109, No. 43, pp. 17615-17620; www.pnas.org/cgi/doi/10.1073/pnas.1206432109.

Christian Riehle and Johann Bauersachs., "Small animal models of heart failure", ESC European Society of Cardiology, Cardiovascular Research (2019) 115, pp. 1838-1849.

Ingrid E. Scheffer et al., "ILAE classification of the epilepsies: Position paper of the ILAE Commission for Classification and Terminology", *Epilepsia*, 58(4), 2017, pp. 512-521.

Robert S. Fisher et al., "Operational classification of seizure types by the International League Against Epilepsy: Position Paper of the ILAE Commission for Classification and Terminology", *Epilepsia*, 58(4): 2017, pp. 522-530.

Iori Ohmori et al., "Novel animal model of combined generalized and focal epilepsy", *Epilepsia*. 2022;63, pp. e80-e85.

Ludmyla Kandratavicius et al., "Animal models of epilepsy: use and limitations", Neuropsychiatric Disease and Treatment, 2014:10, Sep. 9, 2014, pp. 1693-1705.

\* cited by examiner

Sequence analysis result of Txn1 gene in mutant rat

Fig.2

|  |  | 48　　　54　　　　　66 |  |
|---|---|---|---|
| 1 | Rattus norvegicus (Rat) | KYSNVVFLEVDVDDCQDVA | (SEQ ID NO:3) |
| 2 | Mus musculus (Mouse) | KYSNVVFLEVDVDDCQDVA | (SEQ ID NO:4) |
| 3 | Nannospalax Galili (Blind mole rat) | KYSNVVFLEVDVDDCQDVA | (SEQ ID NO:5) |
| 4 | Carlito Syrichta (Tarsier monkey) | KYSNVVFLEVDVDDCQDVA | (SEQ ID NO:6) |
| 5 | Peromyscus Maniculatus (Rodent) | KYSNVVFLEVDVDDCQDVA | (SEQ ID NO:7) |
| 6 | Bos Mutus (Cattle) | KYSNVVFLEVDVDDCQDVA | (SEQ ID NO:8) |
| 7 | Ovis Aries (Sheep) | KYSNVVFLEVDVDDCQDVA | (SEQ ID NO:9) |
| 8 | Pteropus Alecto (Bat) | KYSNVVFLEVDVDDCQDVA | (SEQ ID NO:10) |
| 9 | Rousettus Aegyptiacus (Fruit bat) | KYSNVVFLEVDVDDCQDVA | (SEQ ID NO:11) |
| 10 | Galeopterus Variegatus (Lemur) | KYSNVVFLEVDVDDCQDVA | (SEQ ID NO:12) |
| 11 | Vicugna Pacos (Alpaca) | KYSNVVFLEVDVDDCQDVA | (SEQ ID NO:13) |
| 12 | Odobenus Rosmarus Divergens | KYSNVVFLEVDVDDCQDVA | (SEQ ID NO:14) |
| 13 | Acinonyx Jubatus (Cheetah) | KYSNVVFLEVDVDDCQDVA | (SEQ ID NO:15) |
| 14 | Mustela Putorius Furo (Ferret) | KYSNVVFLEVDVDDCQDVA | (SEQ ID NO:16) |
| 15 | Balaenoptera Acutorostrata Sca | KYSNVVFLEVDVDDCQDVA | (SEQ ID NO:17) |
| 16 | Sus Scrofa (Pig) | KYSNVVFLEVDVDDCQDVA | (SEQ ID NO:18) |
| 17 | Macaca Mulatta (Rhesus monkey) | KYSNVVFLEVDVDDCQDVA | (SEQ ID NO:19) |
| 18 | Colobus Angolensis Palliates | KYSNVVFLEVDVDDCQDVA | (SEQ ID NO:20) |
| 19 | Ceratotherium Simum Simum | KYSNVVFLEVDVDDCQDVA | (SEQ ID NO:21) |
| 20 | Callithrix Jacchus (Marmoset) | KYSNVVFLEVDVDDCQDVA | (SEQ ID NO:22) |
| 21 | Propithecus Coquereli (Sifaka) | KYSNVVFLEVDVDDCQDVA | (SEQ ID NO:23) |
| 22 | Camelus Ferus (Camel) | KYSNVVFLEVDVDDCQDVA | (SEQ ID NO:24) |
| 23 | Manis Javanica (Pangolin) | KYSNVVFLEVDVDDCQDVA | (SEQ ID NO:25) |
| 24 | Ursus Maritimus (White bear) | KYSNVVFLEVDVDDCQDVA | (SEQ ID NO:26) |
| 25 | Miniopterus Natalensis (Vesper bat) | KYSNVVFLEVDVDDCQDVA | (SEQ ID NO:27) |
| 26 | Cavia Porcellus (Guinea pig) | KYSNVVFLEVDVDDCQDVA | (SEQ ID NO:28) |
| 27 | Aotus Nancymaae (Night monkey) | KYSNVVFLEVDVDDCQDVA | (SEQ ID NO:29) |
| 28 | Tursiops Truncatus (Dolphin) | KYSNVVFLEVDVDDCQDVA | (SEQ ID NO:30) |
| 29 | Ailuropoda Melanoleuca (Giant panda) | KYSNVVFLEVDVDDCQDVA | (SEQ ID NO:31) |
| 30 | Equus Caballus (Horse) | KYSNVVFLEVDVDDCQDVA | (SEQ ID NO:32) |
| 31 | Bos Taurus (Cattle) | KYSNVVFLEVDVDDCQDVA | (SEQ ID NO:33) |
| 32 | Acinetobacter Sp MII | KYSNVIFLEVDVDDCQDVA | (SEQ ID NO:34) |
| 33 | Homo Sapiens | KYSNVIFLEVDVDDCQDVA | (SEQ ID NO:35) |
| 34 | Nomascus Leucogenys (Gibbon) | KYSNVIFLEVDVDDCQDVA | (SEQ ID NO:36) |
| 35 | Octodon Degus (Degu) | KYSNVLFLEVDVDDCQDVA | (SEQ ID NO:37) |
| 36 | Ictidomys Tridecemlineatus | KYSNVLFLEVDVDDCQDVA | (SEQ ID NO:38) |
| 37 | Marmota Marmota Marmota (Marmot) | KYSNVLFLEVDVDDCQDVA | (SEQ ID NO:39) |
| 38 | Chinchilla Lanigera (Chinchilla) | KYSNVLFLEVDVDDCQDVA | (SEQ ID NO:40) |
| 39 | Eptesicus Fuscus (Big brown bat) | KYSNVLFLEVDVDDCQDVA | (SEQ ID NO:41) |
|  |  | ***:*********** |  |

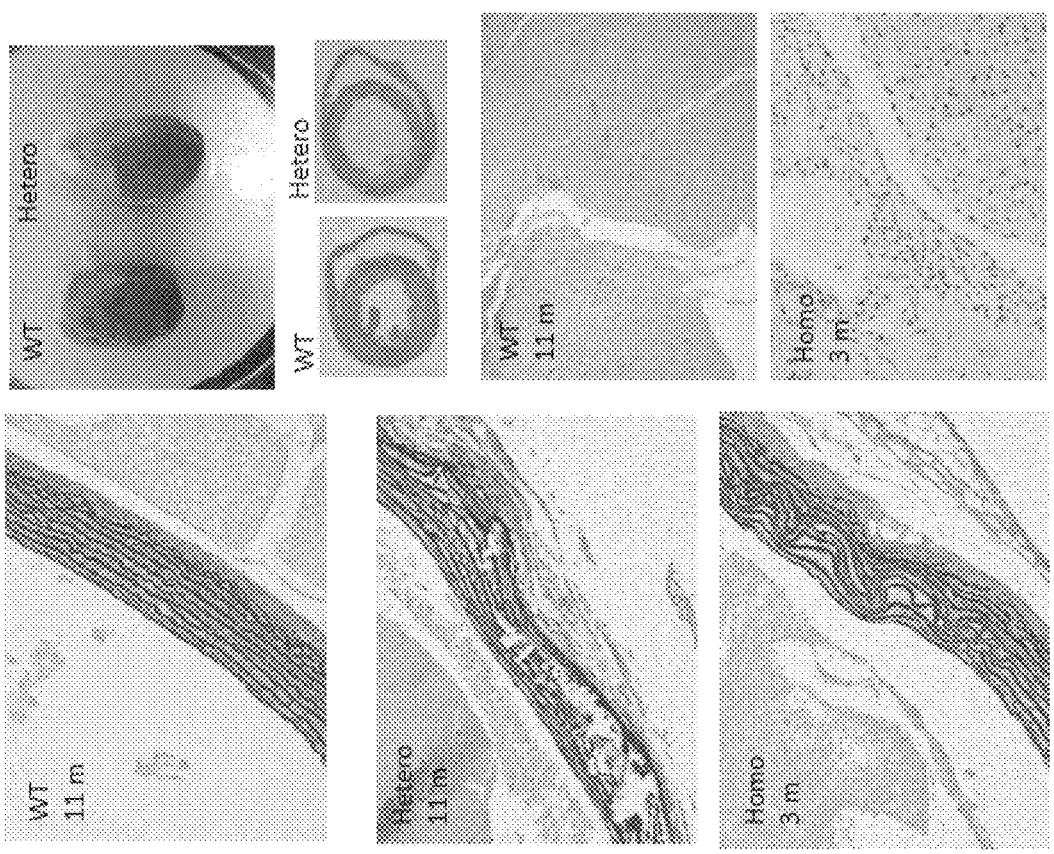
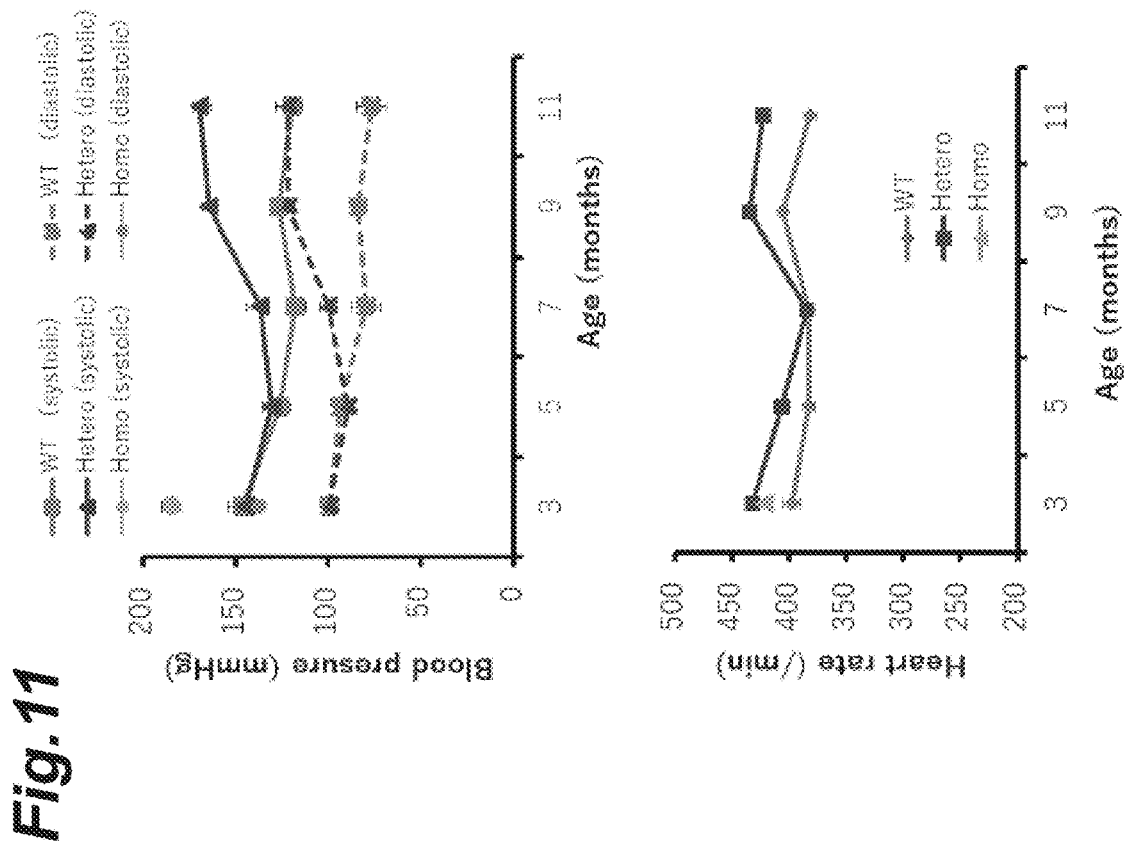
Fig. 11

Fig.16
A
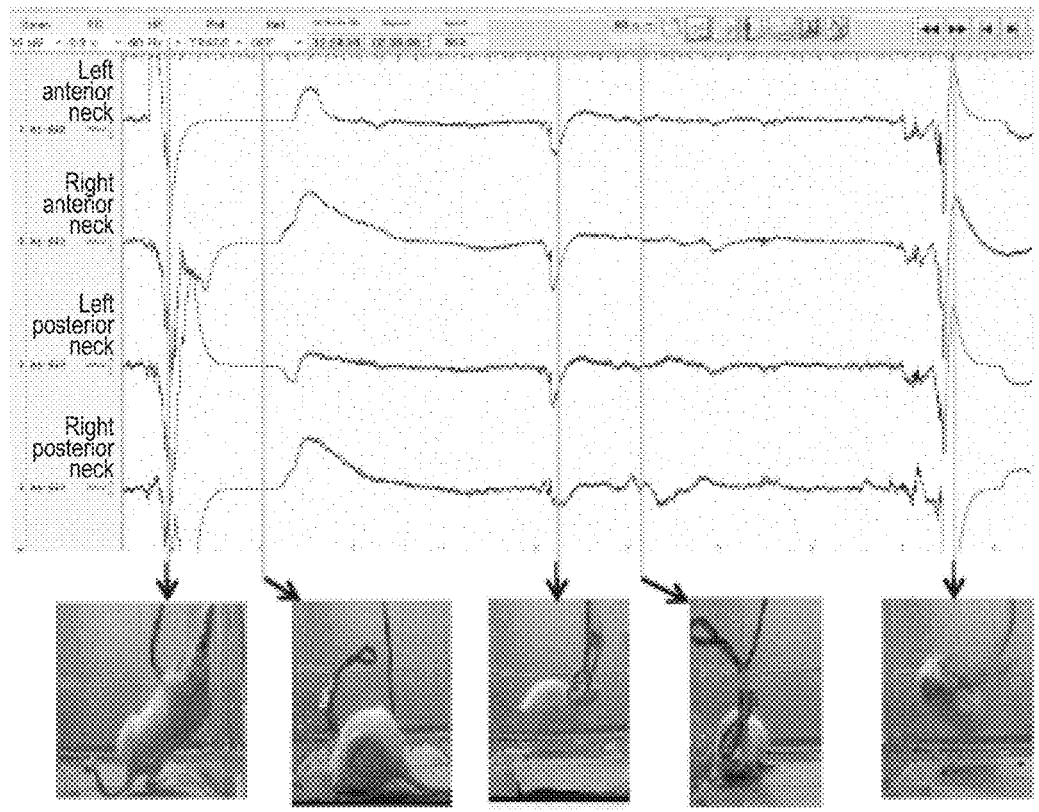
B
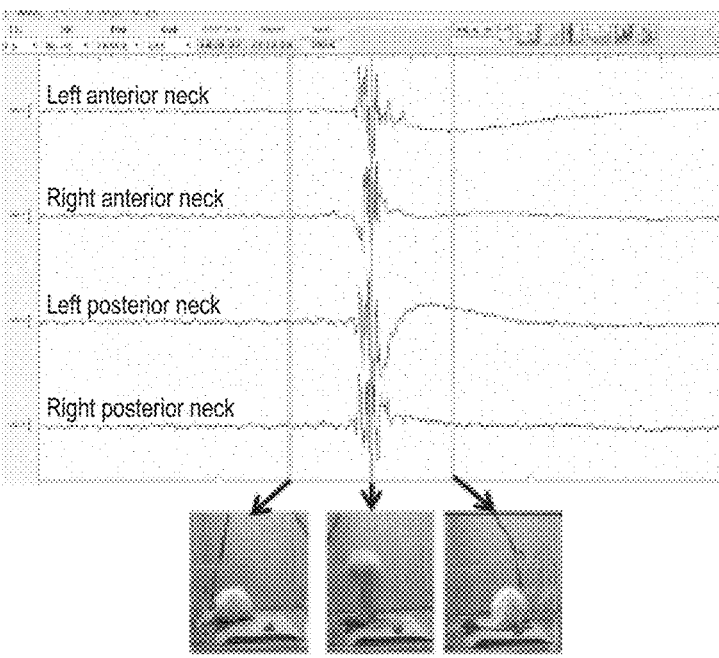
C
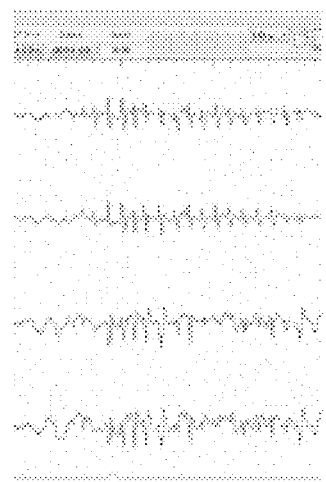

Fig.18
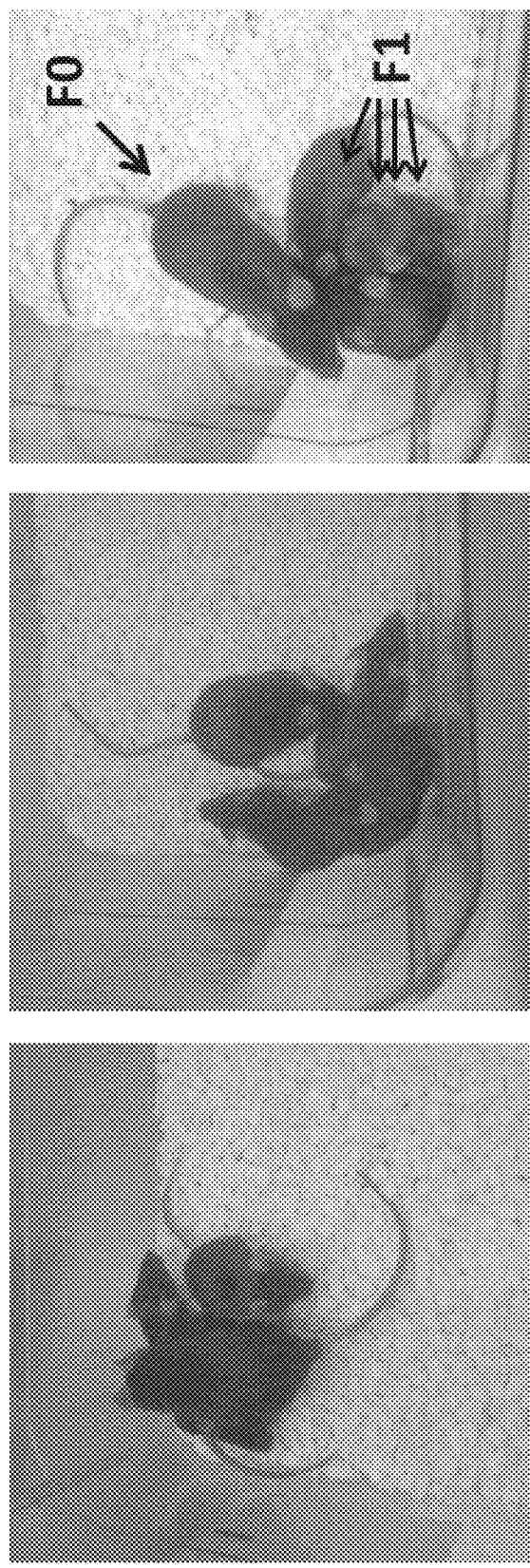
Homozygous genetically modified mouse F0 (about 14 week-old) and its offspring F1 (heterozygous, about 3 week-old)
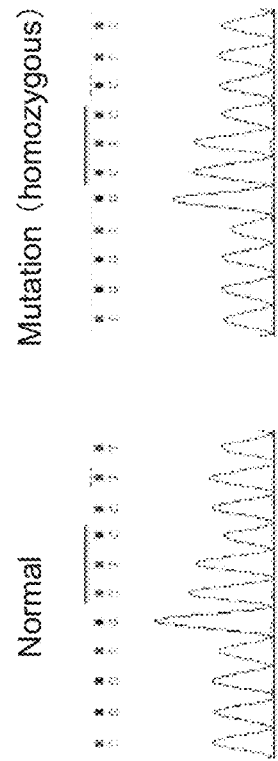
Sequence analysis result of Txn1 gene in homozygous genetically modified mouse

GENETICALLY MODIFIED RAT THAT EXPRESSES AN F54L Txn1 MUTANT

REFERENCE TO A SEQUENCE LISTING

The instant application contains a sequence listing which has been submitted in ASCII format via EFS-Web and is hereby incorporated by reference in its entirety. Said ASCII copy, created on Jun. 10, 2020 is named Sequence_Listing_046884_603070_ST25.txt and is 11,332 bytes in size.

TECHNICAL FIELD

The present invention relates to a non-human model animal useful as a disease research animals that oxidative stress is involved deeply, in particular, useful as a model animal for aging, kidney disease, cardiovascular disease, high blood pressure, aortic dissection, chronic obstructive pulmonary disease, age-dependent epilepsy, dyslipidemia, anemia, osteoporosis, immune disorder, and particularly relates to a non-human model animal in which a gene encoding thioredoxin is modified.

BACKGROUND ART

The living body is equipped with the antioxidant ability by antioxidant enzymes and antioxidants, and there is a system (redox regulation) that maintains homeostasis by adapting to various oxidative stress by controlling the redox state of the living body. However, if this control mechanism cannot sufficiently process the oxidative stress caused by the endogenous or extrinsic factors of the living body, or if the control mechanism fails for some reasons, various obstacles appear in the living body. Excessive oxidative stress damages DNA, proteins, lipids, etc., causing cell dysfunction and cell death, and is therefore considered to be one of the important causes in cancer and aging.

Thioredoxin is a protein with a molecular weight of about 12 kDa consisting of 105 amino acids in human, rat and mouse, and has two cysteine residues in its active site. The dithiol/disulfide exchange reaction between the cysteine residues contributes to the redox reaction of the substrate. The reduced thioredoxin bearing dithiol reduces the disulfide bond of a substrate protein and becomes itself in oxidized form.

Thioredoxin is induced by various factors such as ultraviolet light, radiation, oxidants, viral infection, ischemia-reperfusion injury, administration of anti-cancer agents, etc., which are factors that cause oxidative stress, and it regulates transcription factors that regulate various gene expression and the activity of intracellular signaling molecules (J. Annual Review of Immunology. 15, 351-369 (1997), Annual Review of Biophysics and Biomolecular Structure 30, 421-455 (2001)). Thioredoxin acts defensively against oxidative stress-induced diseases, is resistant to various chemical substances and anticancer agents, and thioredoxin expression is involved in longevity (J Gerontol A Biol Sci Med Sci., 66A: 1286-1299 (2011), The Journal of Clinical Investigation 112 (9), 1395-1406 (2003), Nephrol Dial Transplant; 22: 1547-1557 (2007)). As a conventional technique, a thioredoxin-deficient mouse has been created, but this defective gene homozygous mouse died in the fetal period, and the heterozygote was normal (Non-Patent Document 1). In addition, there is a transgenic animal that expresses a thioredoxin gene having a dominant negative effect in the heart and serves as a hypertrophic cardiomyopathy model (Non-patent Document 2).

CITATION LIST

Non Patent Literature

[Non-Patent Document 1] Developmental Biology 178, 179-185 (1996)
[Non-Patent Document 2] J Clin Invest. 112, 1395-1406 (2003)

SUMMARY OF INVENTION

Technical Problem

The problem to be solved is the absence of non-human animal models of various diseases caused by diminished thioredoxin function. The object of the present invention is to provide a non-human animal model applicable for aging, kidney disease, cardiovascular disease, hypertension, aortic dissection, chronic obstructive pulmonary disease, age-dependent epilepsy, dyslipidemia, anemia, osteoporosis, immune abnormality, etc.

Solution to Problem

The present invention provides a non-human animal model applicable as a disease model such as aging kidney disease, cardiovascular disease, hypertension, aortic dissection, chronic obstructive pulmonary disease, age-dependent epilepsy, dyslipidemia, anemia, osteoporosis, immune disorder, etc. caused by hypofunction of thioredoxin. In order to solve the above-mentioned problems, the present inventors administered to male rats ethylnitrosourea, a chemical mutagen which randomly induces point mutations on the genome, and produced an offspring rat group by mating with female rats, selected rats with phenotypic abnormalities from the group, and confirmed gene abnormalities to find out for the first time that the causative gene was a mutation in the Txn1 gene. As a result of further studies, the present inventors succeed in the production of a non-human animal having mutations in the Txn1 gene, which can be born even if homozygous, and applicable as a disease model such as aging, kidney disease, cardiovascular disease, hypertension, chronic obstructive pulmonary disease, age-dependent epilepsy, dyslipidemia, anemia, osteoporosis, immune disorder, and the present invention has been completed.

That is, the present invention is, consists of the following.
1. A non-human model animal in which a gene encoding thioredoxin is modified.
2. The non-human model animal according to item 1 above, wherein the modified gene encoding thioredoxin decrease an amount of NADPH (nicotinamide adenine dinucleotide phosphate) consumed per unit time to reduce a disulfide bond of a substrate protein and a decrease rate thereof is in a range of 10% to 90%.
3. The non-human model animal according to item 1 or 2 above, wherein the animal is adapted as a disease model selected from the group consisting of aging, kidney disease, cardiovascular disease, hypertension, aortic dissection, chronic obstructive pulmonary disease, age-dependent epilepsy, dyslipidemia, anemia, osteoporosis and immune disorder.

4. A method for screening a drug, wherein the method uses the non-human model animal according to any one of items 1 to 3 above.

Advantageous Effects of Invention

The non-human model animal of the present invention in which the gene encoding the thioredoxin is modified shows disease such as aging, kidney disease, cardiovascular disease, hypertension, aortic dissection, chronic obstructive pulmonary disease, age-dependent epilepsy, dyslipidemia, anemia, osteoporosis, immune disorder, and can be used as a model animal for elucidating the pathological conditions of these diseases and screening therapeutic agents.

BRIEF DESCRIPTION OF DRAWINGS

FIG. 2 is a diagram showing alignment analysis with amino acid (48-66th positions) in the vicinity of the Txn1 gene mutation site (F at 54th position) in Txn1 gene-modified rats with other animal species.

FIG. 11 shows cardiovascular disease in wild type and genetically modified rats. It shows blood pressure measurement data and photographs of rupture of media of large blood vessel, irregular fiber, calcification, and myocardial dilation. (Experimental Example 7).

FIG. 16 shows electroencephalograms showing the state of epileptic seizures in Txn1 gene-modified rats. (Experimental Example 12).

FIG. 18 shows photographs of a Txn1 gene-modified mouse produced by a genome editing technique using the CRISPR/Cas9 system and a diagram showing the results of sequence analysis of the Txn1 gene. It shows genetically modified mouse F0-#3 (homozygous type; mother, about 14-week-old) and its four offspring F1 mice (heterozygous type; 3 males, 1 female; about 3-week-old), and a sequence analysis of Txn1 gene in F0-#3 mouse. It was confirmed that the 54th codon TTC of the Txn1 gene was changed to CTC, and as a result, the 54th amino acid phenylalanine (F) was replaced with leucine (L). (Experimental Example 14)

DESCRIPTION OF EMBODIMENTS

Figure 1:
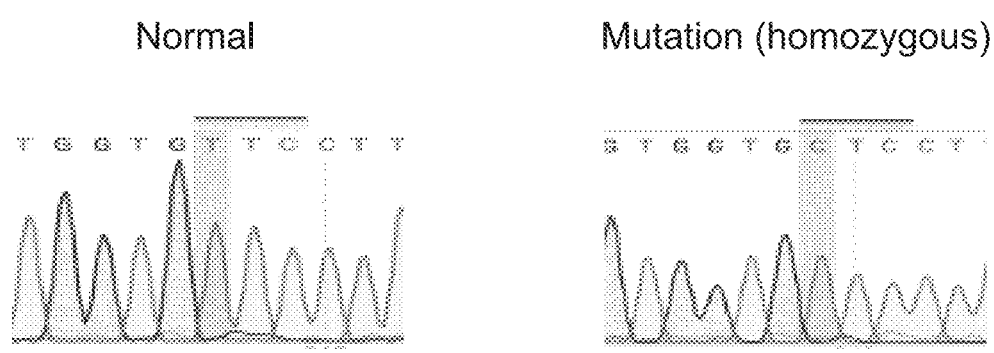
FIG. 1 is a diagram showing the results of sequence analysis of mutations in the Txn1 gene of rats showing phenotypic abnormalities. Regarding the rat, it was confirmed that the 54th codon TTC of the Txn1 gene was changed to CTC, and as a result, the 54th amino acid phenylalanine (F) was replaced with leucine (L). (Example 1).
Figure 3:
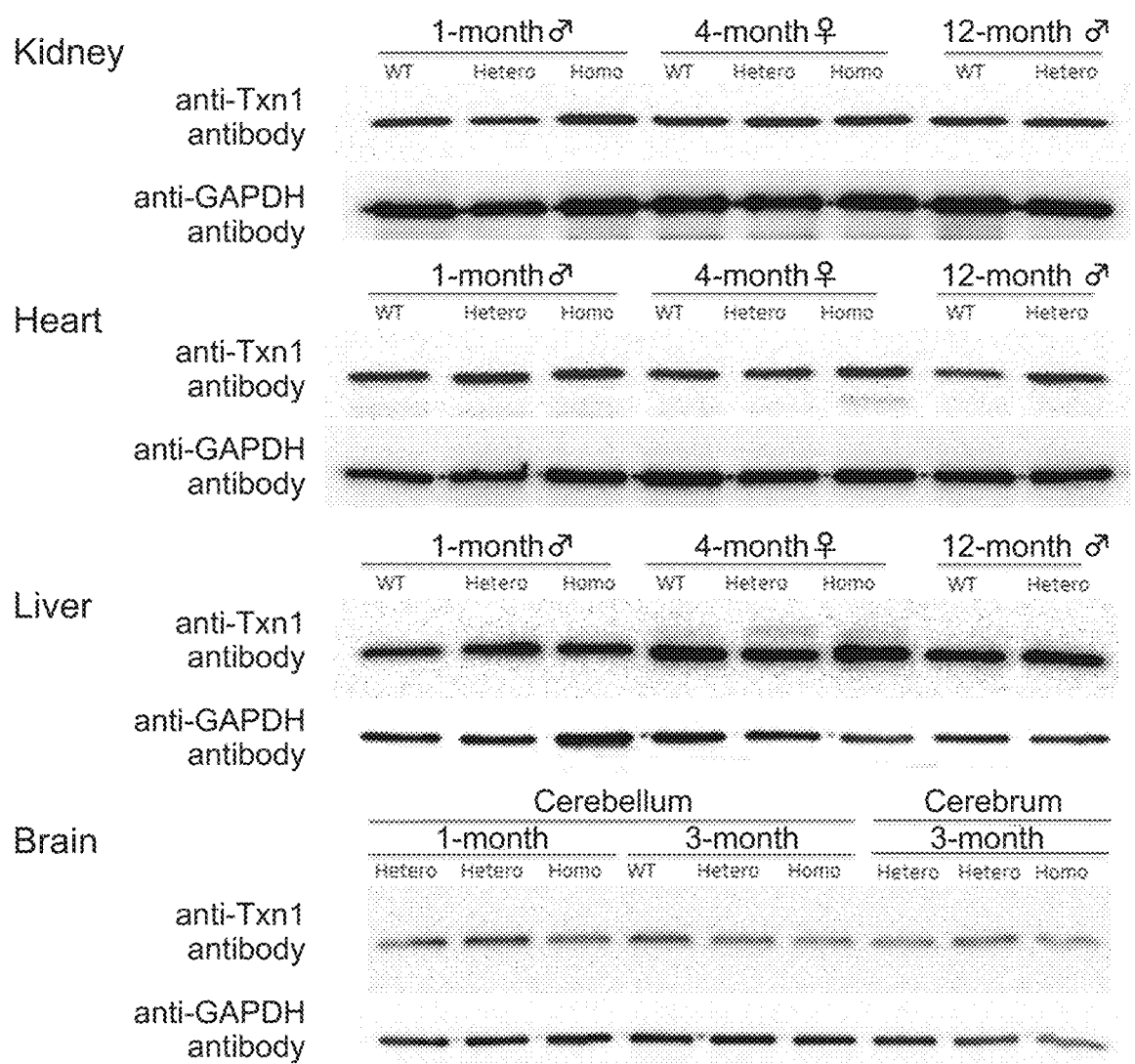
FIG. 3 is a diagram showing that thioredoxin encoded by the Txn gene is expressed in multiple organs throughout the body (kidney, heart, liver, brain). (Experimental Example 1).

The non-human model animal of the present invention is a non-human model animal of a disease that develops due to a decrease in the function of thioredoxin due to a modified gene encoding thioredoxin. Examples of the non-human model animal of the present invention include mammals other than humans, and examples thereof include monkeys, marmosets, cows, pigs, dogs, cats, guinea pigs, rabbits, rats and mice. In particular, rodents such as rats, mice, and guinea pigs are preferable because they are easy to handle, and among them, rats are preferable.

The non-human model animal of the present invention is a non-human model animal obtained by modifying the gene encoding thioredoxin. Thioredoxin is a protein having a molecular weight of about 12 kDa consisting of 105 amino acids in human, rat and mouse, and has two cysteine residues in its active site. It contributes to the redox reaction of the substrate by a dithiol/disulfide exchange reaction between the cysteine residues. The reduced thioredoxin having dithiol reduces disulfide bonds of substrate proteins and becomes itself in oxidized form. The gene encoding thioredoxin is any gene called TXN, TRX, TRX1, TRDX, Txn1, Txn, Trx1 or ADF. For example, human-derived genes are called TXN, TRX, TRX1 or TRDX, rat-derived genes are called Txn1 or Txn, and mouse-derived genes are called Txn1, Txn, Trx1 or ADF. As a gene encoding thioredoxin, for example, the rat-derived gene Txn1 includes the gene specified by the nucleotide sequence shown in GenBank Accession No. NM_053800 (SEQ ID NO: 1), and the Txn1 protein is specified by the amino acid sequence shown in SEQ ID NO: 2.

(SEQ ID NO: 1)
ATGGTGAAGCTGATCGAGAGCAAGGAAGCTTTTCAGGAGGCC

CTGGCCGCTGCGGGAGACAAGCTTGTGGTAGTGGACTTCTCT

GCCACGTGGTGTGGACCTTGCAAAATGATCAAGCCCTTCTTTC

ATTCCCTCTGTGACAAGTATTCCAATGTGGTGTTCCTTGAAGT

AGACGTGGATGACTGCCAGGATGTTGCTGCAGACTGTGAAGT

CAAATGCATGCCGACCTTCCAGTTCTATAAAAAGGGTCAAAA

GGTTGGGGAGTTCTCTGGTGCTAACAAGGAAAAGCTCGAAGC

CACTATTACGGAGTTTGCCTAA (SEQ ID NO: 2)
MVKLIESKEAFQEALAAAGDKLVVVDFSATWCGPCKMIKPFFH

SLCDKYSNVVFLEVDVDDCQDVAADCEVKCMPTFQFYKKGQK

VGEFSGANKEKLEATITEFA

The non-human animal model of the present invention in which the gene encoding thioredoxin is modified in each of homozygous model and heterozygous model shows disease such as aging, kidney disease, cardiovascular disease, hypertension, aortic dissection, chronic obstructive pulmonary disease, age-dependent epilepsy, dyslipidemia, anemia, osteoporosis, and immune disorders. Hereinafter, the modified gene is also simply referred to as "modified thioredoxin gene". The modified thioredoxin gene according to the present invention may reduce the reducing function of substrate protein on which thioredoxin acts to 10% to 90%, preferably 10% to 70%, more preferably 26.9% to 53.9%. Since the consumption of C35S thioredoxin was reduced to 2.55% to 7.45%, the functionally reduced range of the modified thioredoxin gene in the present invention is a value excluding the range which C35S shows reduction. The modified thioredoxin gene may have a nucleotide sequence capable of expressing thioredoxin in which the 54th amino acid F is replaced with L. Such nucleotide sequences includes, in addition to the nucleotide sequence encoding thioredoxin in which the 54th codon TTC is modified to CTC, any nucleotide sequence encoding a protein having the same amino acid sequence as the modified thioredoxin due to the degeneracy of the gene codon.

The genetically modified non-human model animal of the present invention may be any animal that can express a modified thioredoxin by a nucleotide sequence (modified thioredoxin gene) encoding thioredoxin on the genome of the animal. Such animals can be achieved by placing the modified thioredoxin gene on the genome. For example, it can be produced by artificially changing the genetic information of an individual using genetic engineering. Examples of genetically modified non-human model animals include transgenic animals into which a specific gene has been externally introduced, and knock-in animals in which a specific gene has been replaced. In addition, it can be prepared by genome editing of a model animal by introducing, deleting, replacing a gene in the chromosome thereof further in combination with an effector.

A transgenic non-human animal generally refers to a non-human animal in which an exogenous gene called a transgene is artificially integrated into the host genome and is inherited for generations. It is often produced for the purpose of expressing a mutant protein different from the protein possessed by the host. As a method for producing a transgenic non-human, a method known per se, for example, a microinjection method can be adopted. It is possible to introduce the modified thioredoxin gene of the present invention into the pronucleus of a fertilized egg collected from a donor animal, transplant the fertilized egg into the oviduct of the recipient animal, and spontaneously give birth to produce a transgenic non-human animal. The transgenic non-human animal of the present invention can be prepared by introducing the modified thioredoxin gene of the invention into unfertilized eggs, fertilized eggs, progenitor cells including sperm and its primordial germ cells, etc., preferably at the stage of embryogenesis in the development of non-human animals (more preferably, in the single cell before cleavage of the fertilized egg or at the cleavage stage and generally before the 8-cell stage), using calcium phosphate method, electric pulse method, lipofection method, agglutination method, microinjection method, particle gun method, DEAE-dextran method, and the like. In addition, a transgenic non-human animal can be produce also by that the modified thioredoxin gene of the present invention is introduced into somatic cells, living organs, tissue cells and the like by the gene transfer method to prepare cell cultures, tissue cultures and the like and these cells are fused with the germline precursor cells described above by a cell mixing method known per se.

The fertilized egg into which the gene has been introduced is then transplanted into the oviduct of a foster mother to become a fetus, and DNA is extracted from a part of the body (for example, the tip of the tail for mice and rats) at the age of 3- to 4-weeks after birth and the presence of the transgene can be confirmed by Southern analysis or PCR. If the individual confirmed to have the transgene is the first generation, the transgene is transmitted to its offspring (F1). Furthermore, by crossing this F1 individual with a wild-type animal or another F1 animal, an individual (F2) having a transgene in one (heterozygous) or both (homozygous) of the diploid chromosome can be prepared.

According to another embodiment, the non-human animal of the present invention that expresses thioredoxin in which the 54th amino acid F is replaced by L can be produced also by introducing the modified thioredoxin gene of the present invention described above into ES cells (embryonic stem cells). For example, it can be prepared by introducing the modified thioredoxin gene of the present invention into HPRT-negative (hypoxanthine guanine phosphoribosyl transferase gene-deficient) ES cells derived from normal rat blastocysts. ES cells in which the modified thioredoxin gene of the present invention is integrated on the rat endogenous gene are selected by the HAT selection method. Then, the selected ES cells are microinjected into a fertilized egg (blastocyst) obtained from another normal non-human animal. The blastocyst is transplanted into the uterus of another normal non-human animal as a foster mother. Then, a chimeric transgenic non-human animal is born from the foster parent non-human animal. A heterozygous transgenic non-human animal can be obtained by mating the chimeric transgenic non-human animal with a normal non-human animal. By mating the heterozygous transgenic non-human animals with each other, homozygous transgenic non-human animals can be obtained. It can be said that these transgenic non-human animals are model animals in which the gene encoding thioredoxin of the present invention is modified.

According to another embodiment, a knock-in non-human animal expressing thioredoxin in which the 54th amino acid F is replaced with L can be prepared by introducing the modified thioredoxin gene of the present invention into ES cells. For example, it can be prepared by introducing the modified thioredoxin gene of the present invention into ES cells of a normal non-human animal such as rat. ES cells in which the modified thioredoxin gene of the present invention is substituted on the endogenous gene of a non-human animal are selected by the positive selection method using G418 and the negative selection method using the herpes thymidine kinase gene. Then, the selected ES cells are microinjected into a fertilized egg (blastocyst) obtained from another normal non-human animal. The blastocyst is transplanted into the uterus of another normal non-human animal as a foster mother. Then, a chimeric knock-in non-human animal is born from the foster mother non-human animal. A heterozygous knock-in rat can be obtained by mating the chimeric knock-in non-human animal with a normal non-human animal. A homo knock-in non-human animal can be obtained by mating the heterozygous knock-in rats. It can be said that these knock-in non-human animals are non-human model animals in which the gene encoding thioredoxin of the present invention is modified.

In yet another aspect, the non-human model animal of the present invention can also be produced by using the technique of genome editing. As a method of genome editing, a method known per se or any method developed in the future can be applied. For example, gene-specific disruption or knock-in of a target gene in a model animal is performed by a technique such as CRISPR/Cas system, Transcription Activator-Like Effector Nucleases (TALEN), Zinc Finger Nuclease (ZFN), and the like to produce non-human model animals.

EXAMPLES

Hereinafter, for a better understanding of the present invention, details of the contents of the present invention will be described by examples and experimental examples.

(Example 1) Production of Txn1 Gene-Modified Rat

In this example, rats with phenotypic abnormalities are analyzed, and the production of the Txn1 gene-modified rats based on the analysis results is described.

1) Confirmation of Rat with Phenotypic Abnormalities

Ethyl nitrosourea (N-ethyl-N-Nitorosourea; ENU), a chemical mutagen which induces random point mutations in the genome (40 mg/kg) was intraperitoneally administered to male rats F344/NSlc twice (at the time of 9- or 10-week-old), and the rats were mated with female rats F344/NSlc to produce offspring rats. Rats with phenotypic abnormalities were selected from the offspring rats, and genes involved in phenotypic abnormalities were searched. As a gene analysis, a backcross group was produced by mating with a wild type, and linkage analysis with the disease type was performed using a DNA polymorphism marker on all chromosomes. This narrowed down the relevant loci involved in phenotypic abnormalities, and identified that the causative gene was a mutation of Txn1 gene by genome sequence analysis using a next-generation sequencer. FIG. 1 shows the results of analysis of the thioredoxin Txn1 gene mutation in the rat by sequence analysis using an automatic capillary sequencer (ABI3100). It was confirmed that in rats with the phenotypic abnormalities, the 54th codon TTC of the Txn1 gene was changed to CTC, and as a result, the 54th amino acid F was replaced by L (F54L).

The amino acids in the vicinity of thioredoxin mutation site of the rat (54th F) were aligned and analyzed with other animal species. The 54th amino acid F was conserved across animal species (FIG. 2). This suggests that the 54th F is an important amino acid in the function of the thioredoxin protein, and that the mutation from F to L may play an important role in phenotypic abnormalities.

2) Production of Txn1 Gene-Modified Rat

Rats in which the 54th codon TTC of Txn1 gene was changed to CTC confirmed in 1) above were backcrossed with wild type (WT) rats of the same strain for more than ten generations to match the genetic background with WT, to produce Txn1 gene-modified rats (heterozygotes: Hetero). By crossing the heterozygous Txn1 gene-modified rats with each other, homozygous Txn1 gene-modified rats, heterozygous Txn1 gene-modified rats and wild-type rats (WT) were obtained. In the following experiments, this sibling WT was used as a control. Hereinafter, the homozygous mutant rat is referred to as "Homo" and the heterozygous mutant rat is referred to as "Hetero". Wild-type rat (WT) is referred to as "WT". The same applies to the following experimental examples.

(Experimental Example 1) Txn1 Protein Expression Analysis in Txn1 Gene-Modified Rat Txn1 protein expression was confirmed in Txn1 gene-modified rats prepared in Example 1. Kidney, heart, liver and brain tissues were excised from One-month-old and 4-month-old WT, Hetero and Homo, and 12-month-old WT and Hetero, frozen in liquid nitrogen and stored in a deep freezer. Protein was extracted from each tissue using Lysis Buffer, and subjected to ultrasonication. After removing the precipitate with a cooling centrifuge and measuring the protein concentration, Western blotting was carried out using an anti-Txn1 antibody and an anti-GAPDH antibody as an internal control. It was revealed that there was no significant difference in the expression level of Txn1 protein in each tissue of Hetero and Homo rats compared with WT. From this, it was considered that the mutant Txn1 protein was also stably expressed without degradation.

(Experiment Example 2) Txn1 Activity Measurement Using Recombinant Txn1 Protein

In this experimental example, Txn1 recombinant protein was prepared using the Txn1 gene cDNA of the Homo rat and the WT rat prepared in Example 1, and the Txn1 activity was measured. RNA was extracted from WT and Homo rats, normal type (WT) and mutant type (F54L) cDNA were prepared by RT-PCT, and the cDNA were inserted into pCMV-Tag2B vector having FLAG-tag. Further, a mutant C35S in which the 35th cysteine, the active center of Txn1, was mutated to serine was prepared and introduced into pCMV-Tag2B vector. The sequences of all the prepared plasmids were confirmed by sequence analysis. Each vector (WT, F54L, C35S, Empty vector) was introduced into human normal cultured cells HEK293 to cause gene expression, and then FLAG-fused thioredoxin protein was purified using anti-FLAG antibody beads (Sigma; ANTI-FLAG M2 Agarose Affinity Gel, A2220). After quantifying the protein concentration and comparing and confirming the amount of each protein by Western blot using anti-Txn1 antibody (Cell Signaling Technology, #2298) and anti-FLAG antibody (Sigma, F3165), Thioredoxin Activity Assay Kit (Redoxica, TR-7011K) and a trace spectrophotometer (De Novix, DS-11+) were used to measure the activity of Txn1.

Figure 4:
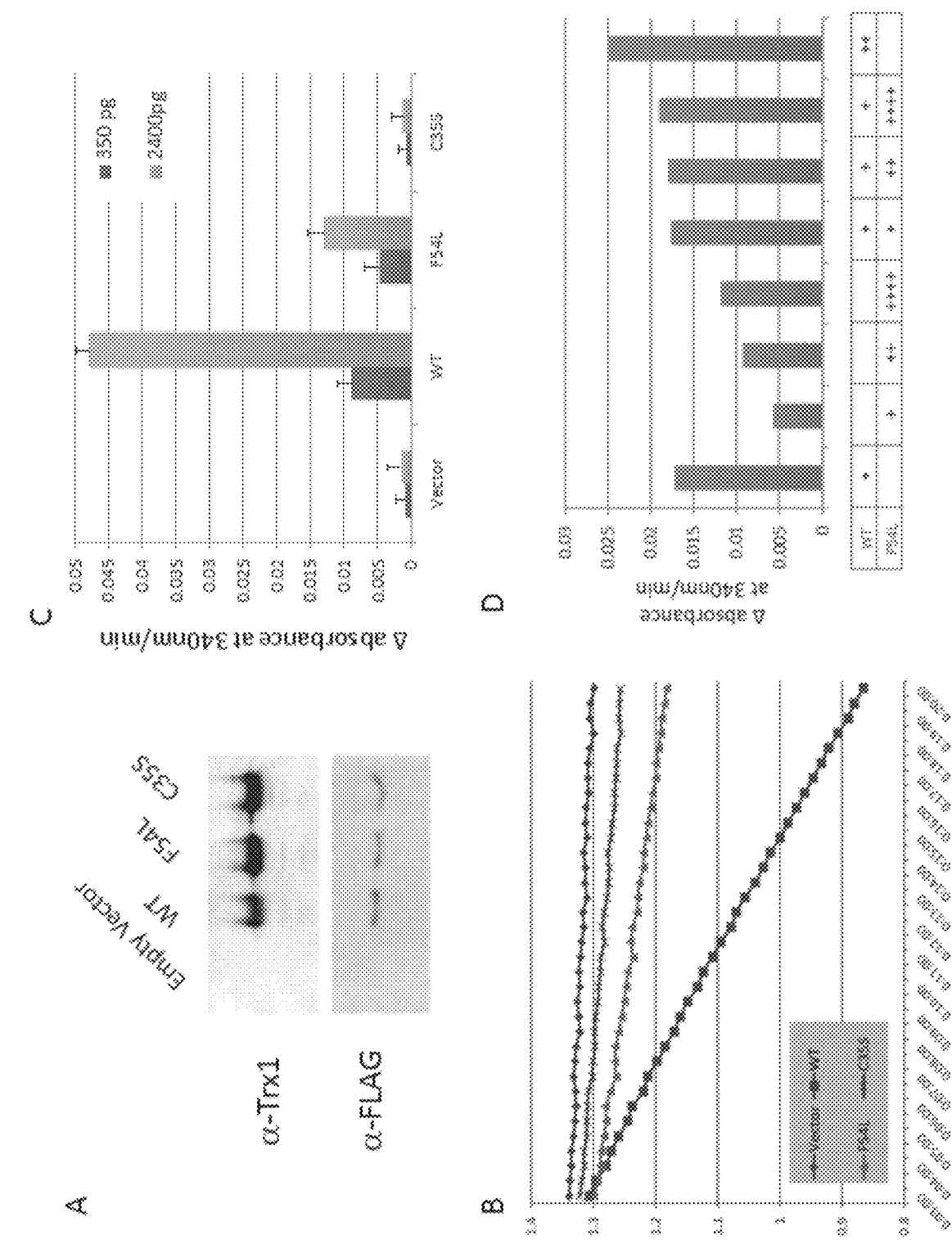
FIG. 4 is a diagram showing a functional analysis of recombinant Txn1 purified protein. A: Wild type, F54L mutant and C35S mutant of thioredoxin protein has been purified. B: NADPH consumed by thioredoxin to reduce disulfide bonds of substrate proteins decreased. C: The amount of NADPH (nicotinamide adenine dinucleotide phosphate) consumed per unit time that is consumed by thioredoxin protein to reduce disulfide bonds of substrate proteins is shown. Compared with the wild type, F54L mutant showed a decrease in consumption of 26.9% to 53.9%, and C35S showed a decrease in consumption of 2.55% to 7.45%. NADPH consumption of F54L mutant is lower than that of the wild type and higher than that of C35S. D: There is no activity inhibition even when wild-type and F54L mutant extracted proteins are mixed, indicating that F54L mutant does not have a dominant negative effect. (Experimental Example 2).

FIG. 4A shows the results of Western blotting using anti-Txn1 antibody and anti-FLAG antibody. FIG. 4B is a diagram showing a decrease in NADPH consumed in order for Txn1 to reduce disulfide bonds of substrate proteins. FIG. 4C is a diagram showing the amount of NADPH consumed per unit time by Txn1 protein. Mutant F54L showed a decrease in NADPH consumption per unit time to 26.9% to 53.9% compared to normal WT (350 pg decreased to 53.9%, 2400 pg decreased to 26.9%). The mutant C35S showed a decrease to 2.55% to 7.45%. FIG. 4D shows that the activity of F54L was not inhibited even when the extracted protein of F54L mutant was mixed with normal WT, and that the F54L mutant did not have a dominant negative effect.

(Experimental Example 3) Measurement of Txn1 Activity in Txn1 Gene-Modified Rat

In the present experimental example, proteins were extracted from the tissues of Homo, Hetero, and WT rats prepared in Example 1 and Txn1 activity was measured. Tissues of 4-month-old Homo, Hetero, and WT were extracted, frozen in liquid nitrogen, and stored in a deep freezer. After protein was extracted from kidney tissue using Lysis Buffer and subjected to ultrasonication, the precipitate was removed by a cooling centrifuge and the protein concentration was quantified. After confirming the amount of protein by Western blot using anti-Txn1 antibody (Cell Signaling Technology, #2298), thioredoxin Activity Assay Kit (Redoxica, TR-7011K) and a trace spectrophotometer (DeNovix, DS-11+) was used to measure the activity of Txn1.

Figure 5:
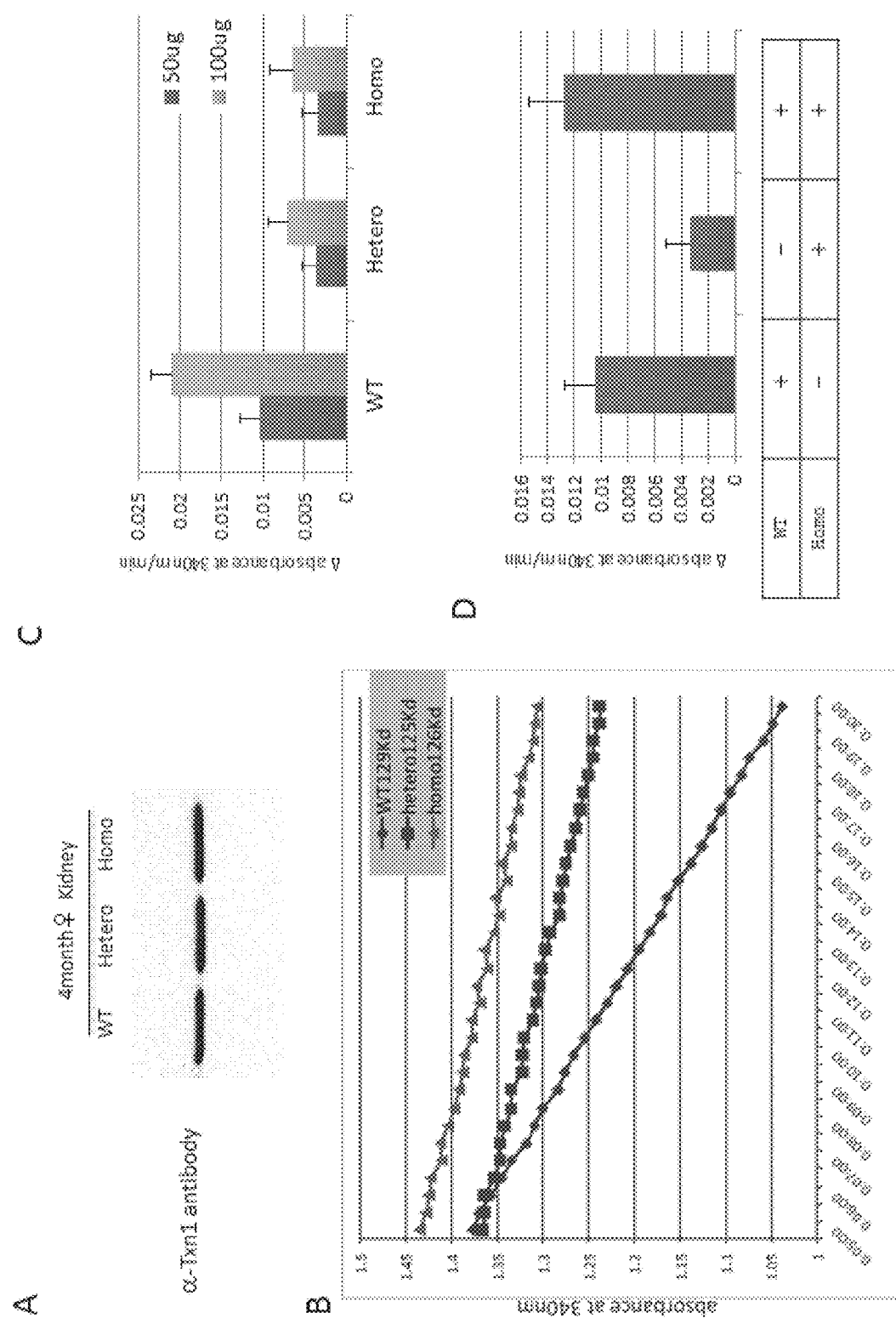
FIG. 5 is a diagram showing a functional analysis of thioredoxin in kidney. A: The protein concentrations of tissue extracts of wild type, F54L mutant heterozygous, F54L mutant homozygous rats are almost identical. B: NADPH consumed by thioredoxin to reduce disulfide bonds of substrate proteins decreased. C: The amount of NADPH consumed per unit time that is consumed by thioredoxin is shown. It is shown that NADPH consumption per unit time by thioredoxin in mutant Hetero rat and Homo rat is lower than that in wild type rat. Compared to wild-type, NADPH consumption pre unit time in mutant showed a decrease of 30.6% to 32.2%. D: There is no activity inhibition even when wild type and Homo extracted proteins are mixed, indicating that F54L mutant has no dominant negative effect. (Experimental Example 3).

FIG. 5A shows the result of Western blotting using anti-Txn1 antibody. It can be seen that the tissue extract protein concentrations of WT, Hetero and Homo rats are almost the same. FIG. 5B is a diagram showing a decrease in NADPH consumed in order for Txn1 to reduce disulfide bonds of substrate proteins. FIG. 5C is a diagram showing the amount of NADPH consumed per unit time by Txn1 measured using 50 µg and 100 µg of extracted proteins. It is shown that the consumption of NADPH per unit time by Txn1 in Hetero and Homo rats is lower than that in WT rats. Compared to WT, Homo showed a decrease in activity of 30.6% to 32.2% (50 µg decreased to 32.2%, 100 µg decreased to 30.6%). FIG. 5D shows the results of Txn1 activity measured using WT extracted proteins 50 µg (WT), Homo extracted proteins 50 µg (Homo), and a mixture of 50 µg WT extracted proteins and 50 µg Homo extracted proteins (WT+Homo). When Homo extracted proteins were mixed with WT extracted proteins, the activity was not inhibited, and it revealed that the F54L mutant had no dominant negative effect.

(Experimental Example 4) Lifespan of Txn1 Gene-Modified Rat

Figure 6:
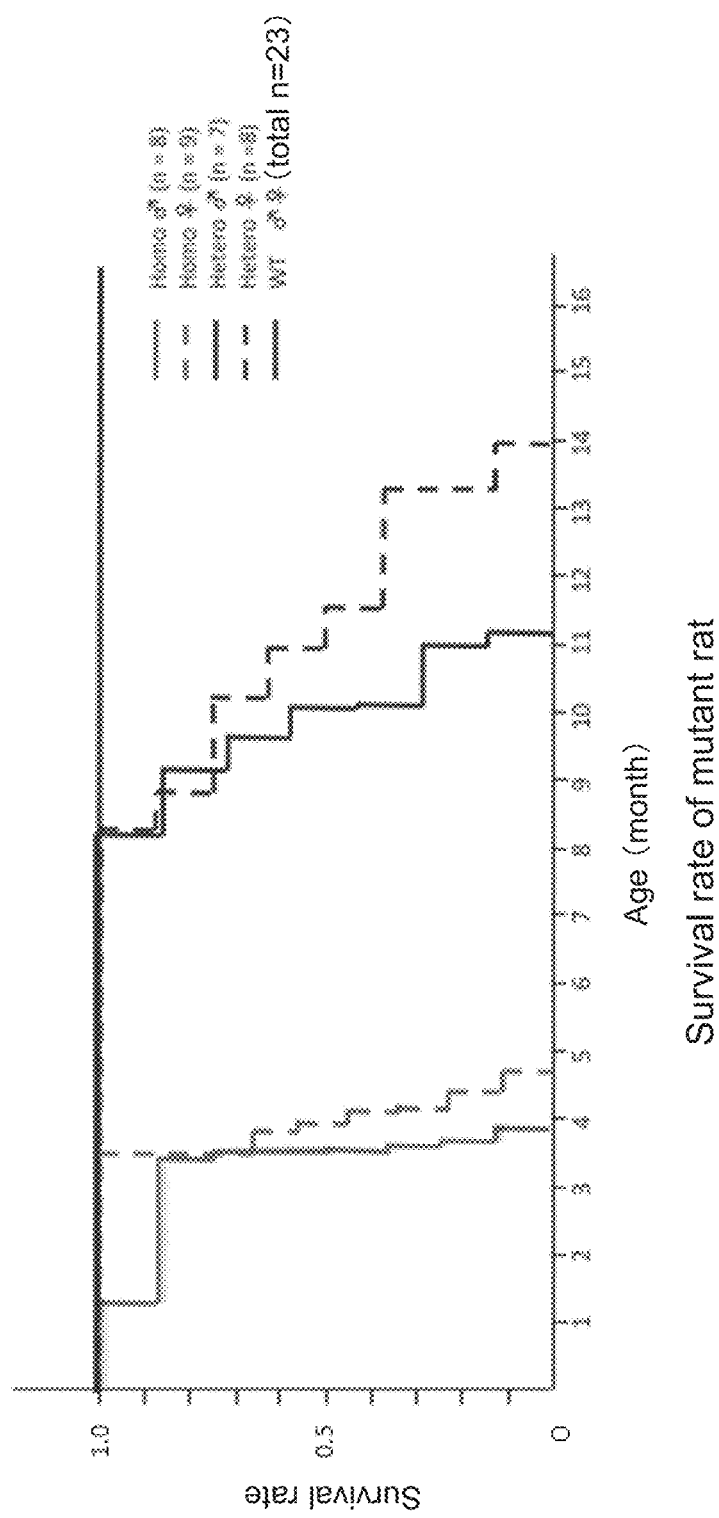
FIG. 6 shows survival curves and sex differences between wild-type and Txn1 gene-modified rats (homozygotes and heterozygotes). In Txn1 gene-modified rats, females had a longer lifespan. (Experimental Example 4).

In this experimental example, the lifespan of the Homo, Hetero and WT rats produced in Example 1 were confirmed. Compared with the lifespan of WT rats of 2 to 3 years, Homo rats died in about 3-4 months, Hetero tended to die from about 9 months, and it was confirmed that Txn1 gene-modified rats have a short lifespan, and male Txn1 gene-modified rats had a shorter lifespan than females due to sex difference (FIG. 6). As a result, the Txn1 genetically altered rats were considered to be useful as animal models for studying sex difference in aging, kidney diseases, cardiovascular disease, hypertension, aortic dissection, chronic obstructive pulmonary disease, age-dependent epilepsy, dyslipidemia, anemia, osteoporosis, and immunological disorders.

Figure 7:
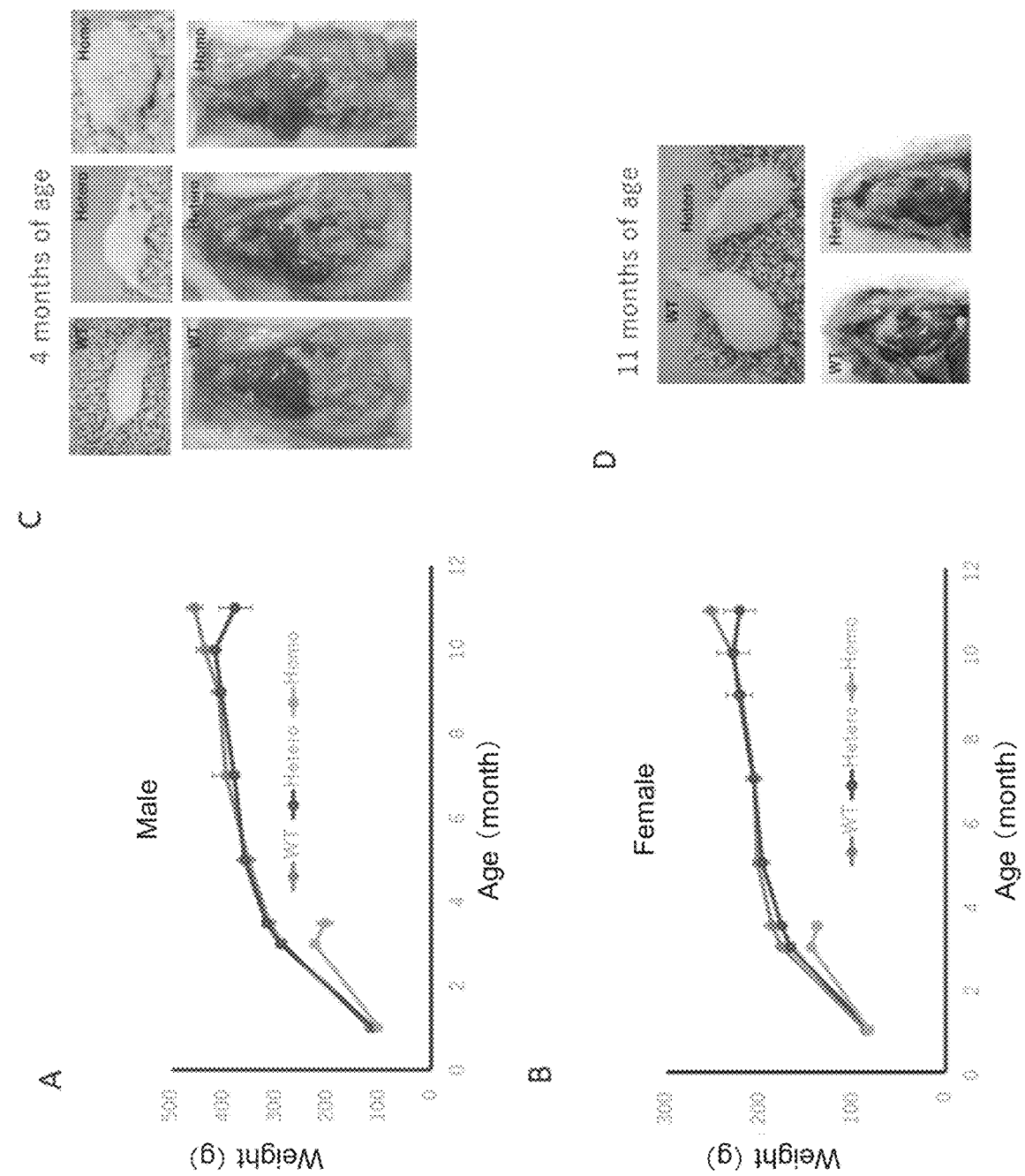
FIG. 7 is a diagram showing the general health status of wild type and Txn1 gene modified rats (homozygotes and heterozygotes). A: Changes in body weight of males were observed, and homozygous mutant rats showed body weight loss after 3 months and heterozygous mutant rats showed weight loss after 11 months. B: Change in body weight of females, and Homo rats showed body weight loss after 3 months and heterozygous mutant rats showed weight loss after 11 months. C: The appearance and gross organ findings at 4 months are shown. Homozygous mutant rats showed marked thinning, spinal deformity, hair loss, visceral fat loss, and thymus atrophy. D: The appearance and gross organ findings at 11 months are shown. Heterozygous mutant rats showed marked thinning, spinal deformity, hair loss, visceral fat loss, and thymus atrophy. (Experimental Example 5).

(Experimental Example 5) Changes in Body Weight and General Health of Txn1 Gene-Modified Rat In this experimental example, the body weight of the Homo, Hetero and WT rats produced in Example 1 was measured over the age of 0 to 12 months, and the health conditions were observed. FIG. 7A is a graph showing changes in body weight of male rats and FIG. 7B is a graph showing changes in body weight of female rats. Weight loss is observed after 3 months in homo rats and after 11 months in hetero rats. FIG. 7C shows the appearance and gross organ findings at the time of 4-month-old. In Homo rats, there is marked thinning, spinal deformity, hair loss, visceral fat loss and thymus atrophy. FIG. 7D shows the appearance and gross organ findings at the time of 11-month-old. In hetero rats, there is marked thinning, spinal deformity, hair loss, visceral fat loss, and thymus atrophy.

Figure 8:
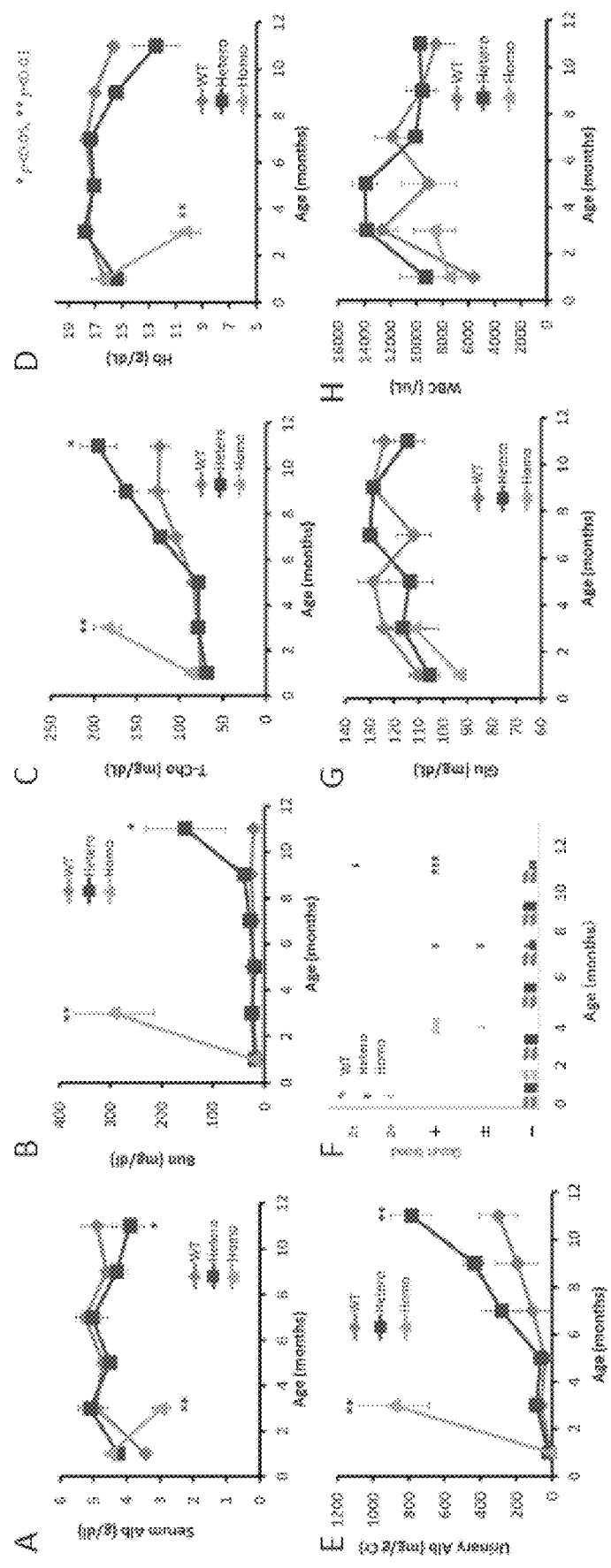
FIG. 8 is a diagram showing progressive renal dysfunction, hypercholesterolemia and anemia in genetically modified rats. A: Serum albumin, B: Blood urea nitrogen (Bun), C: Total cholesterol (T-Cho), D: Hemoglobin (Hb), E: Urinary albumin/Cr amount (Urinary Albumin/Cr), F: urine occult blood, G: blood glucose level (Glucose, Glu) and H: white blood cell count, with each showing change with age. (Experimental Example 6).

(Experimental Example 6) Progressive Renal Dysfunction in Txn1 Gene-Modified Rat In this experimental example, the pathological states of progressive renal dysfunction, hypercholesterolemia, and anemia in the Homo, Hetero and WT rats produced in Example 1 were confirmed. Blood and urine were collected from 0 to 12 month-old rats and subjected to biochemical examination. In FIG. 8, A shows serum albumin, B shows blood urea nitrogen (Bun), C shows total cholesterol (T-Cho), D shows hemoglobin (Hb), E shows urinary albumin amount (Urinary Albumin), F shows urine occult blood, G shows blood glucose level (Glucose, Glu), and H shows the age-related change of white blood cell count. Homo rats had high levels of urinary albumin and Bun at 3-month-old, died of end-stage renal failure at 3 to 4 month-old, and Hetero rats had elevated levels of urinary albumin and Bun from about 7-month-old, and died of end-stage renal failure at about 1-year-old.

Figure 9:
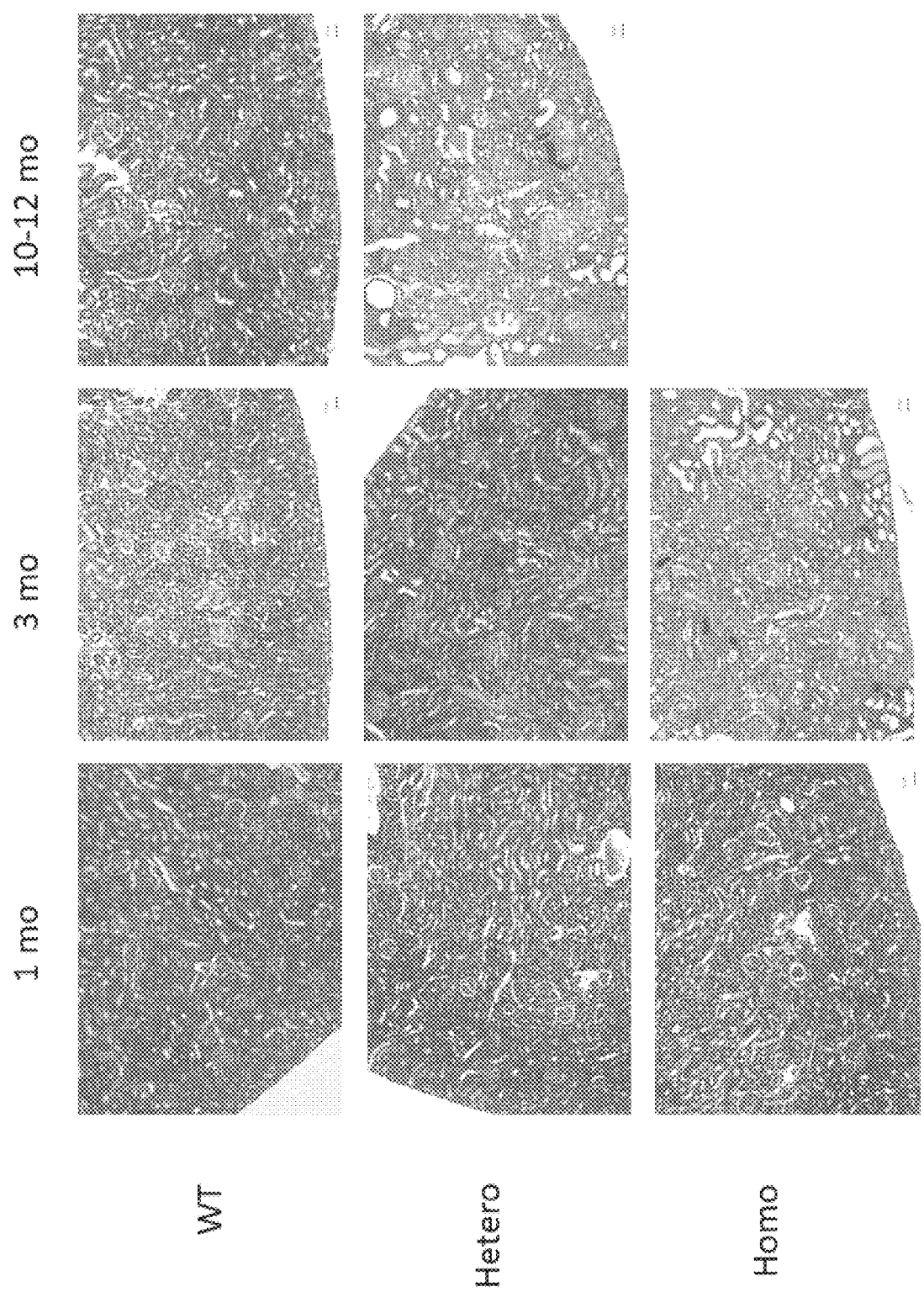
FIG. 9 shows photographs of kidney of wild-type and genetically modified rats stained with Masson trichrome. It shows the progress of fibrosis of the kidney (Experimental Example 6).
Figure 10:
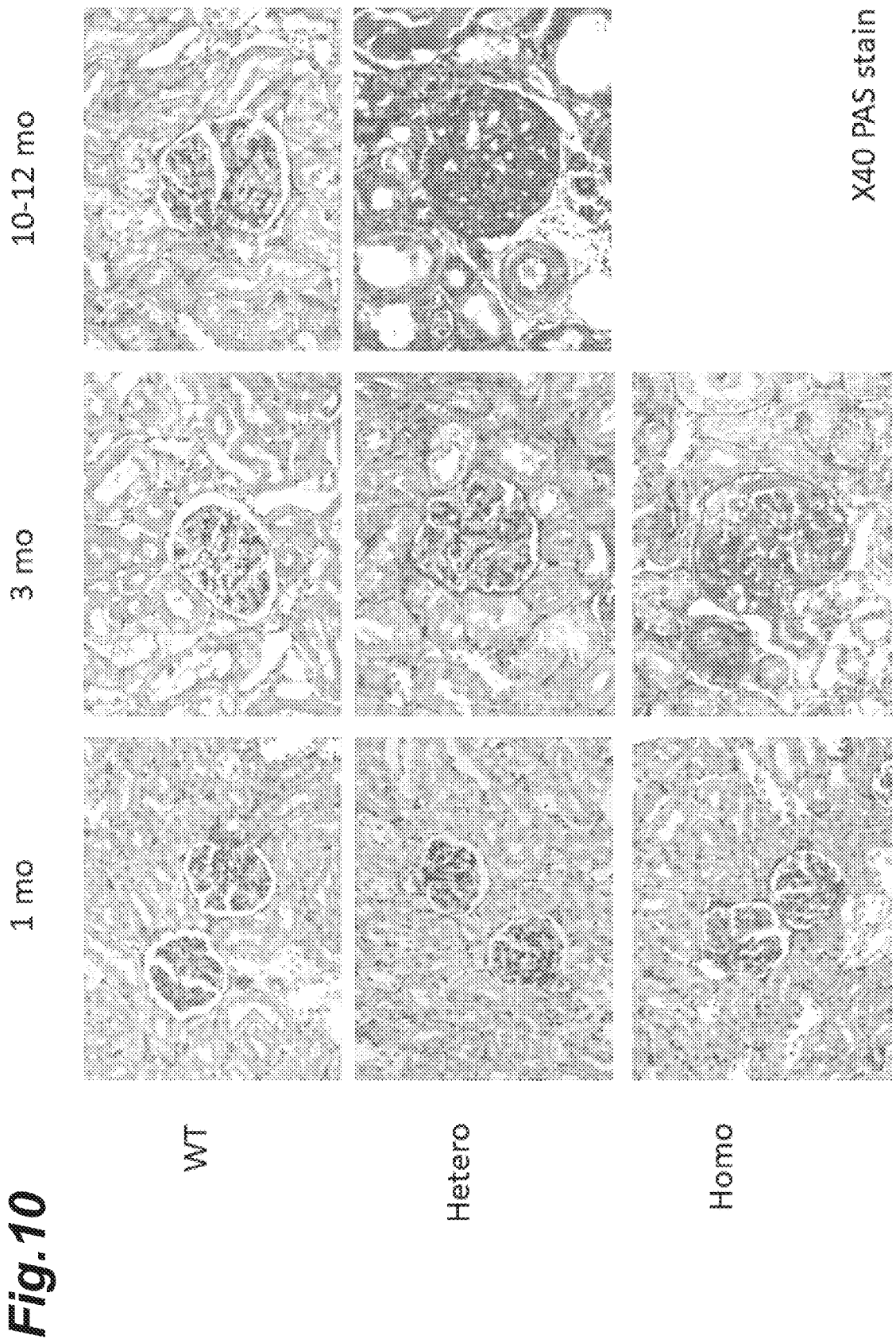
FIG. 10 shows photographs of kidney of wild-type and genetically modified rats stained with PAS (Periodic Acid Schiff). It shows a glomerular lesion and a tubular lesion in a Txn1 gene-modified rat. (Experimental Example 6).

Kidney tissues of WT, Hetero and Homo rats aged 1-month and 3-month, and WT and Hetero rats aged 10 to 12-month were excised and subjected to histopathological analysis. FIG. 9 is a photograph of a kidney section stained with Masson trichrome. It shows the progression of renal fibrosis. FIG. 10 is a photograph of a kidney section stained with Periodic Acid-Schiff (PAS). It shows a glomerular lesion and a tubular lesion in a Txn1 gene-modified rat. That is, glomerulosclerosis, intratubular and extravascular cell proliferation, mesangial cell proliferation, tubular atrophy, tubular dilation, tubular necrosis, and interstitial fibrosis are observed.

The number of dialysis patients due to end-stage renal failure is increasing worldwide, which is a big problem in the medical economy. The number of dialysis patients in Japan was about 300,000 in 2011 (1 out of 450 in the total population). The causes are various, but it is estimated that the number of patients with chronic kidney disease (CKD), a reserve arm of end-stage renal failure, is 12.9% of Japanese adults and 13.3 million people (1 out of 8 adults) is CKD patients requiring intervention. CKD is said to have 5 billion patients worldwide. Background factors of CKD are many lifestyle-related diseases such as diabetes and hypertension, and due to the aging of society, it is expected that the number of patients will increase further in the next 10 years. Since the Txn1 gene-modified rats have a rapid progression of renal dysfunction, it is possible to determine the effect of a therapeutic agent in a short period of time, and in particular, to evaluate the prolongation of life prognosis, which is a clinical problem. Thus it can be used as an excellent model rat for chronic kidney disease. There are many experimentally induced kidney disease models, but the present invention is a hereditary chronic kidney disease model, the chronic kidney disease model rat according to the present invention is superior in that symptoms occur due to spontaneous occurrence without pretreatment of animals unlike other kidney disease models, and that the chronic kidney disease model rat according to the present invention exhibit many renal disease-related complications while the other kidney disease models exhibit only specific symptoms. The rat of the present invention, the cell isolated from the rat of the present invention, and the cell in which the NADPH consumption per unit time of thioredoxin is reduced to 10% to 90% of the normal level are considered to be used not only for studying the elucidation of the mechanism of the pathological condition, but also for the search for biomarkers reflecting the pathological condition, the screening of therapeutic agents and the analysis of drug efficacy.

(Experiment Example 7) Heart Disease in Txn1 Gene-Modified Rat

In this experimental example, the pathology of heart disease in the Homo, Hetero and WT rats produced in Example 1 was confirmed.

FIG. 11 shows cardiovascular diseases in WT, Hetero and Homo rats. The graph on the left shows blood pressure measurement data and heart rate data. In Homo rats, the blood pressure becomes high at 3-month-old, and in Hetero rats, the blood pressure becomes high from about 7-month-old. The center of the graph showed cross sections of large blood vessels of 11-month-old WT and Hetero rats, and 3-month-old Homo rats. Rupture of the tunica media of large vessels, calcification, and irregularities of fibers are observed. On the right, hearts excised from 9-month-old WT and Hetero rats and a tissue section of the fracture surface at the ventricular level are shown. Fibrosis, inflammatory cell infiltration, and myocardial dilation were observed in Hetero and Homo rats.

(Experimental Example 8) Chronic Obstructive Pulmonary Disease in Txn1 Gene-Modified Rat In this experimental example, lesions of chronic obstructive pulmonary disease in Homo, Hetero and WT rats produced in Example 1 were confirmed.

Figure 12:
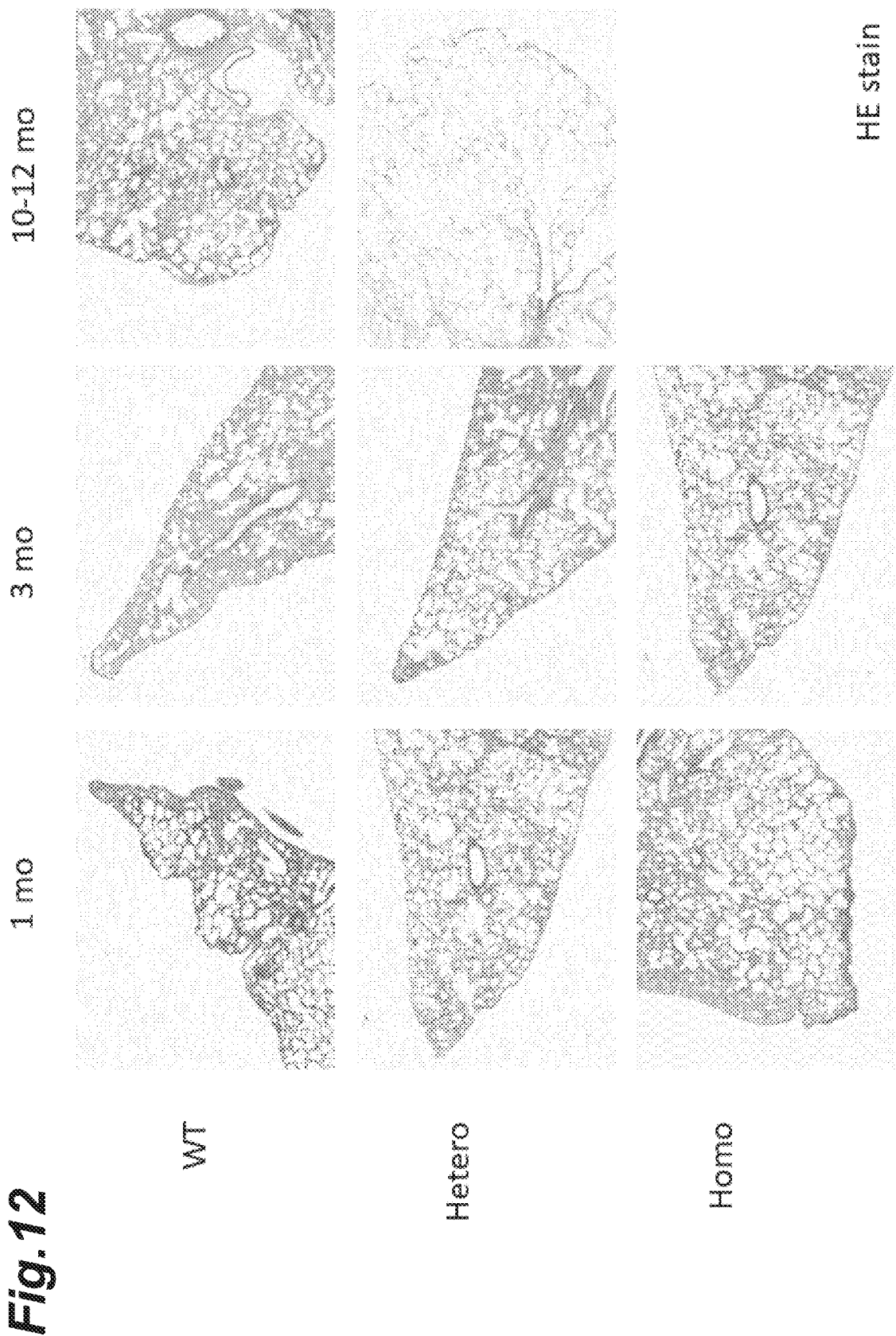
FIG. 12 shows photographs of lung histopathology in wild-type and Txn1 gene-modified rats. (Experimental Example 8).

FIG. 12 shows tissue sections of lungs of Homo, Hetero and WT rats. Compared to WT rats, Hetero and Homo rats showed emphysematous changes. In other words, in the Txn1 gene-modified rats, lymphocyte infiltration of bronchiolar wall and fusion and expansion of alveolar space were observed.

(Experimental Example 9) Thymus Atrophy in Txn1 Gene-Modified Rat

In this experimental example, thymus atrophy in Homo, Hetero and WT rats produced in Example 1 was confirmed. The thymus is a primary lymphoid organ involved in the immune system such as T cell differentiation and maturation, and consists of two lobes called thoracic lobules. Immature lymphocytes are present in the cortex, which is the outer part of the mature thymus, and the inner medulla contains lymphocytes as well as antigen-presenting cells such as macrophages and dendritic cells.

Figure 13:
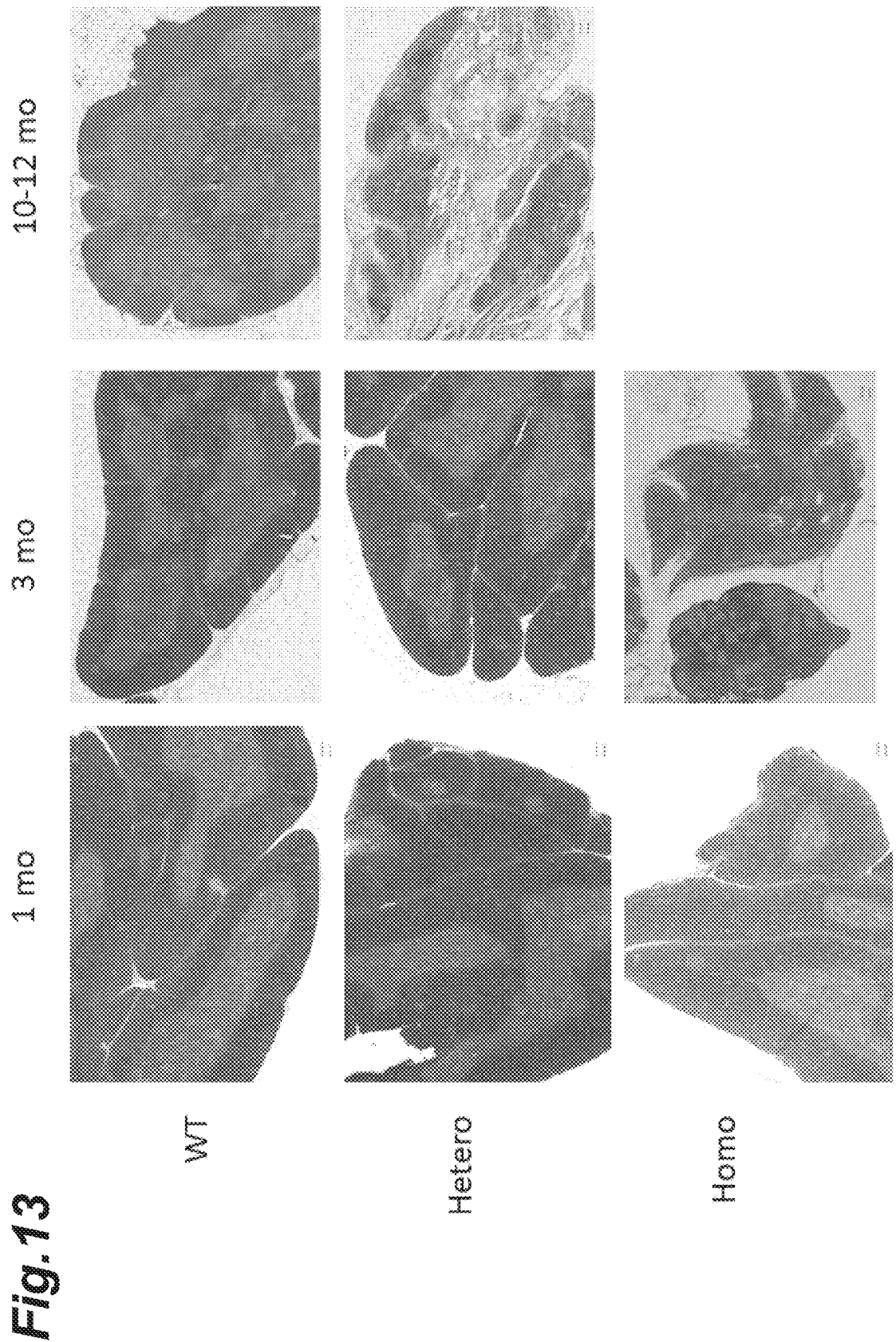
FIG. 13 shows photographs of thymus histopathology in wild-type and Txn1 gene-modified rats. (Experimental Example 9).

FIG. 13 shows tissue sections of thymus of Homo, Hetero and WT rats. The entire thymus of WT rat was stained, whereas fatification and atrophy proceeded in 3-month-old Homo rats and 10- to 12-month old Hetero rats and only a small portion showed thymus tissue. It is said that the thymus begins to become fat with age and atrophy progresses, and it was found that atrophy occurs earlier in Homo and Hetero rats than in WT rats.

(Experimental Example 10) Ovarian Atrophy in Txn1 Gene-Modified Rat

Figure 14:
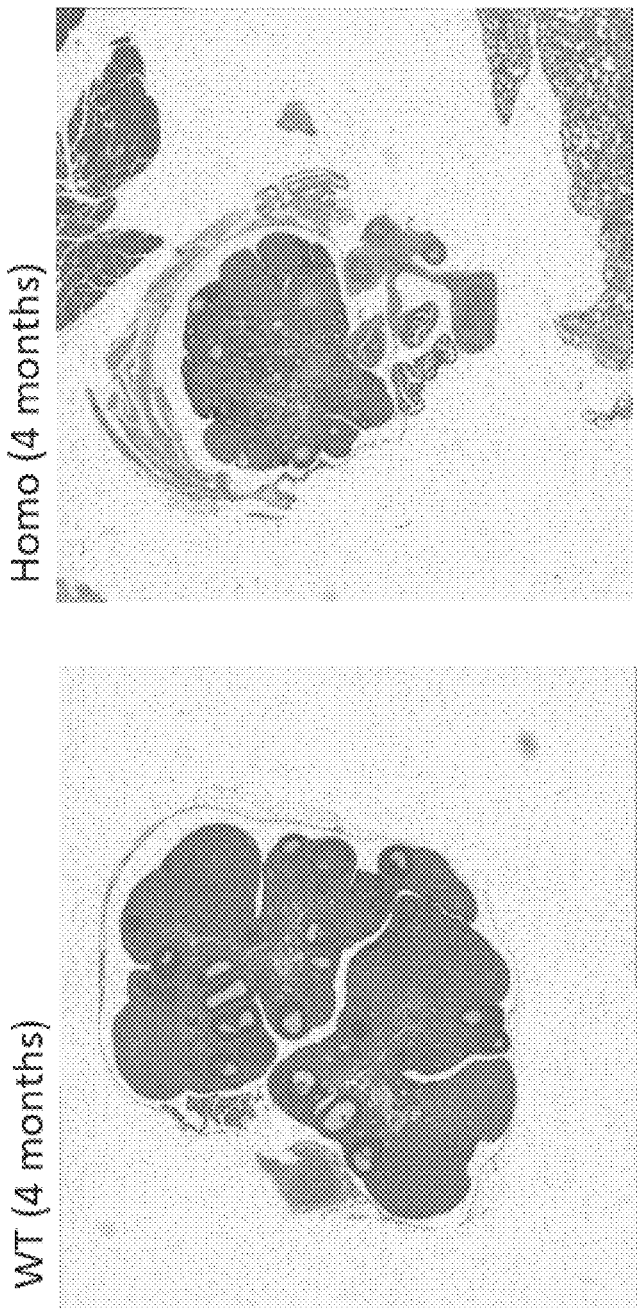
FIG. 14 shows photographs of ovarian atrophy histopathology in wild-type and Txn1 gene-modified rats. (Experimental Example 10).

In the present experimental example, ovarian atrophy in Homo and WT rats produced in Example 1 was confirmed. Ovarian atrophy and a decrease in mature follicles were observed in Homo rats compared to WT rats (FIG. 14).

(Experimental Example 11) Analysis of Bone and Mineral Metabolism in Txn1 Gene-Modified Rat In this experimental example, blood was collected from the Homo, Hetero and WT rats produced in Example 1 at 0- to 12-month-old, subjected to biochemical examination for calcium, inorganic phosphorus, and alkaline phosphatase. In addition, Computed Tomography (CT) was performed on 4-month-old Homo, Hetero and WT rats.

Figure 15:
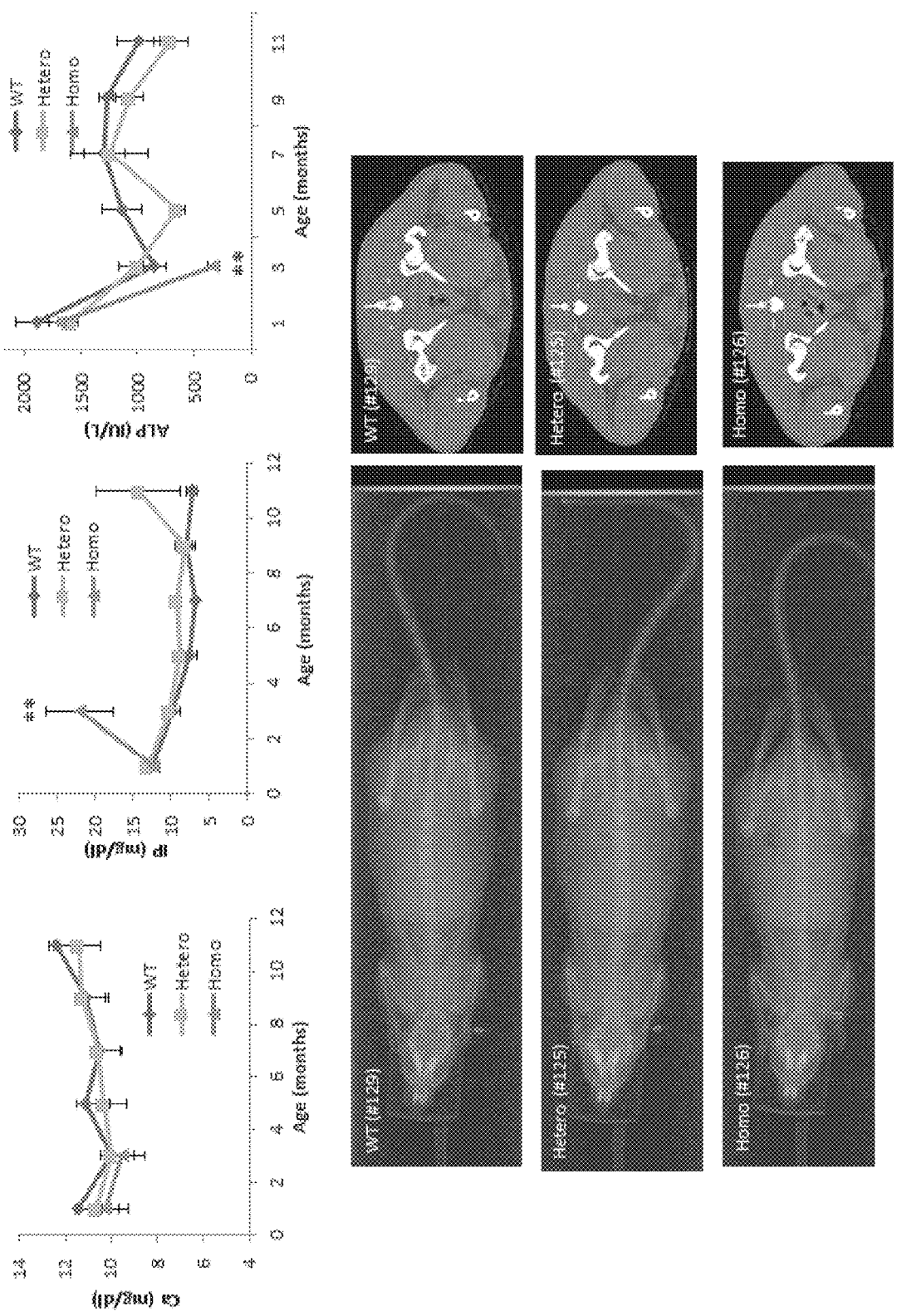
FIG. 15 is a diagram showing bone and mineral metabolism in wild-type and Txn1 gene-modified rats. A: calcium, B: Inorganic phosphorus and C: alkaline phosphatase, with each showing change with age. D: Computed Tomography (CT) images of 4-month-old wild-type and Txn1 gene-modified rats. The left shows the whole image and the right shows the cross-sectional image of the abdomen. (Experimental Example 11).

FIG. 15 shows age changes of calcium (A), inorganic phosphorus (B), and alkaline phosphatase (C). As a result, an increase in inorganic phosphorus (hyperphosphatemia) was observed in 3-month-old Homo rats and in 11-month-old Hetero rats. A decrease in alkaline phosphatase was observed in 3-month-old Homo rats. The overall image is shown on the left of FIG. 15D, and the cross-sectional image of the abdomen is shown on the right. Compared with WT rats, Homo rats were thinner and weaker, and the volume of trunk and lower limb skeletal muscles was decreased.

(Experimental Example 12) Epileptic Seizures in Txn1 Gene-Modified Rats

In this experimental example, epileptic seizures in Homo, Hetero and WT rats produced in Example 1 were confirmed. Epileptic seizures concentrated in 4- to 5-week-old rats and epileptic seizures gradually decreased and disappeared after 6 weeks. More specifically, we confirmed that epileptic seizures changed in age-dependent manner.

Txn1 gene-modified rats exhibited partial seizures, repeated bouncing seizures, and generalized tonic seizures from the age of 4 weeks. FIG. 16A shows simultaneous video electroencephalographic recording of a seizure of a 4- to 5-week-old Hetero rat. The rat repeatedly had seizures where the body suddenly jumps every 20 seconds, and a fast wave and low voltage corresponding to epileptic seizures were observed on the electroencephalogram. Seizures similar to series-forming epileptic spasms of West syndrome in humans were observed. Generalized multiple spike waves appeared during a momentary jumping attack, and a myoclony-like attack (FIG. 16B) was observed. Furthermore, absence-like seizures associated with spike and slow wave complex were observed (FIG. 16C).

Figure 17:
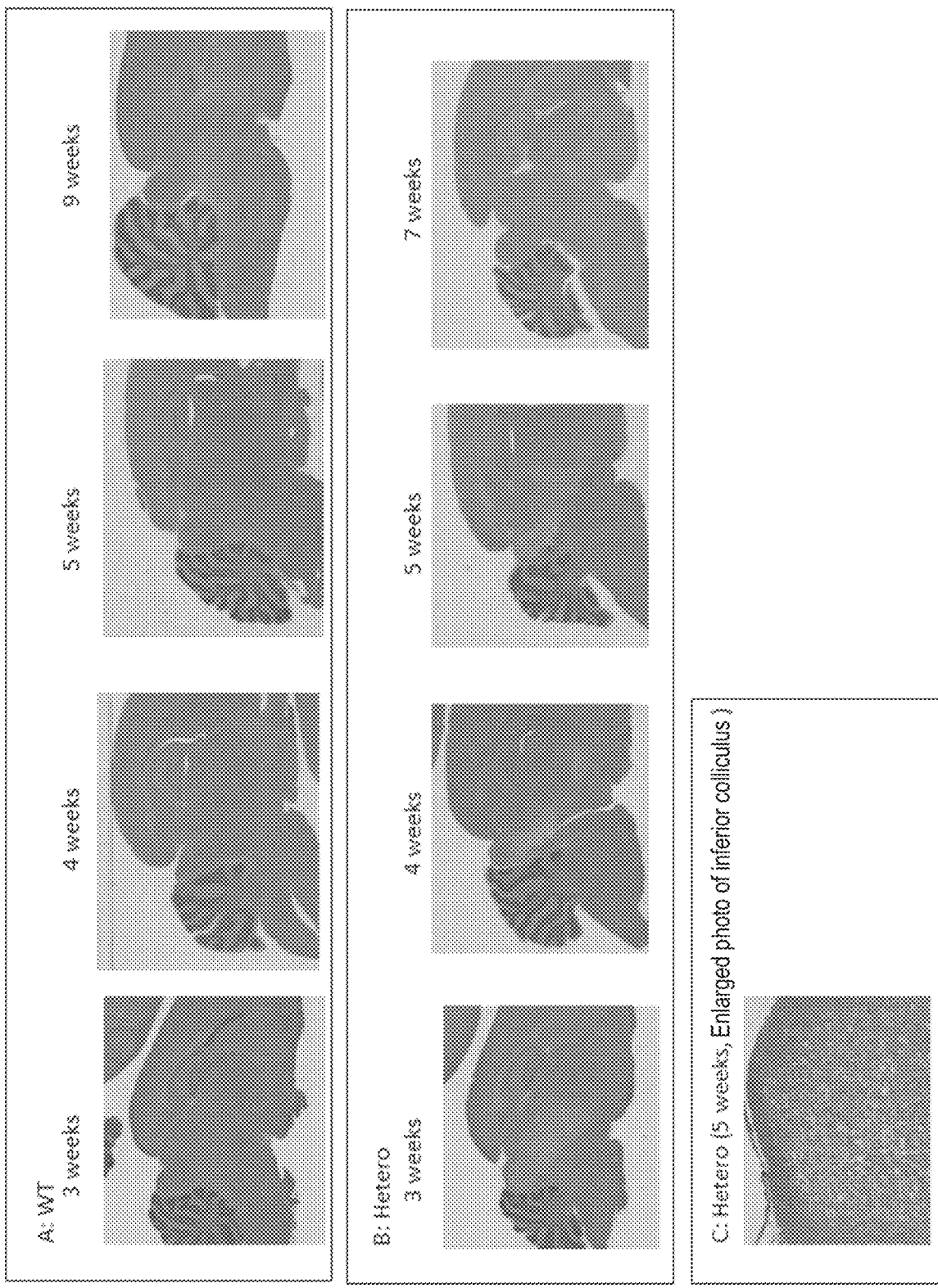
FIG. 17 shows pathological photographs showing a brain lesion in a Txn1 gene-modified rat. (Experimental Example 13).

(Experimental Example 13) Brain Pathological Analysis in Genetically Modified Rat Brain lesions from 3-week-old Txn1 gene-modified rats, before the observation of epileptic seizures, to 4-week-old, 5-week-old, and 7-week-old rats were subjected to pathological examination by HE staining. Three- to five-week-old Hetero rats showed vacuolar degeneration in inferior colliculus, thalamus and hypothalamus (FIG. 17B). This observation was also found in Homo rats, and the lesion site was wider. FIG. 17C shows an enlarged photograph of vacuolar degeneration in inferior colliculus. This degeneration healed in 7-week-old rats (FIGS. 17A and 17B).

Age-dependent epilepsy is an epilepsy syndrome found in childhood. There is a characteristic that the disease type changes with the development of the brain, and onset and age-dependent changes in the disease type are observed at a specific age. This age-dependent change also includes spontaneous healing. Age-dependent epilepsy includes West syndrome, Lennox-Gastaut syndrome, Doose syndrome, childhood absence epilepsy, and benign childhood epilepsy with centrotemporal spikes.

Recently, various causative genes of age-dependent epilepsy have been identified by genetic analysis. Along with this, attempts have been made to produce model animals in epilepsy research facilities around the world, but there are no model animals that reflect the pathology and lesions of age-dependent epilepsy in genetically modified mice and rats. It is considered that the Txn1 gene-modified rat can be used as an excellent age-dependent epilepsy model rat. The rat of the present invention, neurons isolated from the rat of the present invention, and cells in which NADPH consumption of thioredoxin per unit time is reduced to 10% to 90% of the normal level are considered to be useful not only for studying the elucidation of the mechanism of the pathology but also for preventing the onset, screening of therapeutic agents, and drug efficacy analysis.

(Experimental Example 14) Production of Txn1 Gene-Modified Mouse

Txn1 gene-modified mice were created using the CRISPR/Cas9 system. First, a guide RNA containing a sequence near the 54th codon of the mouse Txn1 gene was prepared, and introduced into fertilized eggs of C57BL/6J mice along with Cas9 protein and a single-stranded DNA fragment having a mutant sequence of the 54th codon (including 2 silent mutations). The 136 fertilized eggs that were introduced were transplanted into the uterus of temporary mother. The number of pups F0 born was 9, but 5 died. The remaining 4 animals (F0-#1, F0-#2, F0-#3, F0-#4) were excised at the tail tips, and using the obtained DNA, 363 bases including the 54th codon of the Txn1 gene was amplified by PCR and was subjected to sequence analysis. The above gene-modified mouse F0 was crossed with a C57BL/6J wild type mouse to obtain offspring mouse F1.

The upper part of FIG. 18 is a photograph of F0-#3 mice (homozygous gene-modified mice; female) and its four offspring F1 mice (heterozygous gene-modified mice; 3 males and 1 female). The lower part of FIG. 18 shows a sequence analysis of the Txn1 gene of Txn1 gene-modified mouse F0-#3. It was confirmed that the 54th codon TTC of the Txn1 gene was changed to CTC, and as a result, the 54th amino acid phenylalanine (F) was replaced with leucine (L).

As described in detail above, the non-human model animal of the present invention in which the gene encoding thioredoxin is modified is useful as a disease research animal deeply associated with oxidative stress, particularly, as model animals for aging, kidney disease, cardiovascular disease, chronic obstructive lung, age-dependent epilepsy, dyslipidemia, anemia, osteoporosis, immune disorders, etc. It is also useful for evaluating the effectiveness of health foods and nutritional foods.

The non-human model animal of the present invention in which the gene encoding thioredoxin is modified is useful for the pathological condition analysis of the linkage of a plurality of organ diseases, because the plurality of diseases described above appear. For example, cardiorenal linkage, cardiopulmonary linkage, renal-brain linkage, and the like. In addition, it is useful for evaluating the effects of pharmaceuticals, health foods, etc. on multiple coexisting diseases. It is useful for developments for pharmaceuticals and health foods for human multi-organ disease patients, for example, how pharmaceuticals for heart disease etc. influence/effect co-existing kidney and lung diseases, and how drugs pharmaceuticals for kidney disease etc. influence/effect co-existing heart and brain diseases.

The non-human model animal of the present invention in which the gene encoding thioredoxin is modified can provide each organ, primary cultured cells such as fetal fibroblasts and its cell lines or stem cells, iPS cells derived from the non-human model animal of the present invention. Each cell can be applied to studies and screening of therapeutic agents in aging, kidney disease, cardiovascular disease, chronic obstructive pulmonary disease, age-dependent epilepsy, dyslipidemia, anemia, osteoporosis and the like.

The invention claimed is:

1. A genetically modified rat whose genome comprises a mutation in an endogenous thioredoxin 1 (TXN1) gene, wherein the genetically modified rat expresses an F54L TXN1 mutant and exhibits hypertension, rupture of the tunica media of blood vessels, calcification of blood vessels, fibrosis of a heart, inflammatory cell infiltration of a heart, and myocardial dilation by three months old.

2. The genetically modified rat according to claim 1, wherein the genetically modified rat further exhibits glomerulosclerosis, intratubular and extravascular cell hyperproliferation of the kidney, mesangial cell hyperproliferation, tubular atrophy, dilation, and necrosis of the kidney, and interstitial fibrosis of the kidney by three months old.

3. The genetically modified rat according to claim 2, wherein the genetically modified rat further exhibits age-dependent epilepsy at least by 4- to 5-weeks-old.

4. A genetically modified rat whose genome comprises a mutation in an endogenous thioredoxin 1 (TXN1) gene, wherein the genetically modified rat expresses an F54L TXN1 mutant and exhibits glomerulosclerosis, intratubular and extravascular cell hyperproliferation of the kidney, mesangial cell hyperproliferation, tubular atrophy, dilation, and necrosis of the kidney, and interstitial fibrosis of the kidney by three months old.

5. A genetically modified rat whose genome comprises a mutation in an endogenous thioredoxin 1 (TXN1) gene, wherein the genetically modified rat expresses an F54L TXN1 mutant and exhibits age-dependent epilepsy at least by 4- to 5-weeks-old.

* * * * *

SEQUENCE LISTING

<160> NUMBER OF SEQ ID NOS: 41

<210> SEQ ID NO 1
<211> LENGTH: 318
<212> TYPE: DNA
<213> ORGANISM: Rattus norvegicus

<400> SEQUENCE: 1

```
atggtgaagc tgatcgagag caaggaagct tttcaggagg ccctggccgc tgcgggagac      60
aagcttgtgg tagtggactt ctctgccacg tggtgtggac cttgcaaaat gatcaagccc     120
ttctttcatt ccctctgtga caagtattcc aatgtggtgt tccttgaagt agacgtggat     180
gactgccagg atgttgctgc agactgtgaa gtcaaatgca tgccgacctt ccagttctat     240
aaaaagggtc aaaggttgg ggagttctct ggtgctaaca aggaaaagct cgaagccact     300
attacggagt ttgcctaa                                                   318
```

<210> SEQ ID NO 2
<211> LENGTH: 105
<212> TYPE: PRT
<213> ORGANISM: Rattus norvegicus

<400> SEQUENCE: 2

```
Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Cys Asp Lys
        35                  40                  45

Tyr Ser Asn Val Val Phe Leu Glu Val Asp Val Asp Asp Cys Gln Asp
    50                  55                  60

Val Ala Ala Asp Cys Glu Val Lys Cys Met Pro Thr Phe Gln Phe Tyr
65                  70                  75                  80

Lys Lys Gly Gln Lys Val Gly Glu Phe Ser Gly Ala Asn Lys Glu Lys
                85                  90                  95

Leu Glu Ala Thr Ile Thr Glu Phe Ala
            100                 105
```

<210> SEQ ID NO 3
<211> LENGTH: 19
<212> TYPE: PRT
<213> ORGANISM: Rattus norvegicus

<400> SEQUENCE: 3

```
Lys Tyr Ser Asn Val Val Phe Leu Glu Val Asp Val Asp Asp Cys Gln
1               5                   10                  15

Asp Val Ala
```

<210> SEQ ID NO 4
<211> LENGTH: 19
<212> TYPE: PRT
<213> ORGANISM: Mus musculus

<400> SEQUENCE: 4

```
Lys Tyr Ser Asn Val Val Phe Leu Glu Val Asp Val Asp Asp Cys Gln
1               5                   10                  15

Asp Val Ala
```

<210> SEQ ID NO 5

-continued

```
<211> LENGTH: 19
<212> TYPE: PRT
<213> ORGANISM: Nannospalax Galili

<400> SEQUENCE: 5

Lys Tyr Ser Asn Val Val Phe Leu Glu Val Asp Val Asp Asp Cys Gln
1               5                   10                  15

Asp Val Ala

<210> SEQ ID NO 6
<211> LENGTH: 19
<212> TYPE: PRT
<213> ORGANISM: Carlito Syrichta

<400> SEQUENCE: 6

Lys Tyr Ser Asn Val Val Phe Leu Glu Val Asp Val Asp Asp Cys Gln
1               5                   10                  15

Asp Val Ala

<210> SEQ ID NO 7
<211> LENGTH: 19
<212> TYPE: PRT
<213> ORGANISM: Peromyscus maniculatus

<400> SEQUENCE: 7

Lys Tyr Ser Asn Val Val Phe Leu Glu Val Asp Val Asp Asp Cys Gln
1               5                   10                  15

Asp Val Ala

<210> SEQ ID NO 8
<211> LENGTH: 19
<212> TYPE: PRT
<213> ORGANISM: Bos mutus

<400> SEQUENCE: 8

Lys Tyr Ser Asn Val Val Phe Leu Glu Val Asp Val Asp Asp Cys Gln
1               5                   10                  15

Asp Val Ala

<210> SEQ ID NO 9
<211> LENGTH: 19
<212> TYPE: PRT
<213> ORGANISM: Ovis aries

<400> SEQUENCE: 9

Lys Tyr Ser Asn Val Val Phe Leu Glu Val Asp Val Asp Asp Cys Gln
1               5                   10                  15

Asp Val Ala

<210> SEQ ID NO 10
<211> LENGTH: 19
<212> TYPE: PRT
<213> ORGANISM: Pteropus alecto

<400> SEQUENCE: 10

Lys Tyr Ser Asn Val Val Phe Leu Glu Val Asp Val Asp Asp Cys Gln
1               5                   10                  15

Asp Val Ala

<210> SEQ ID NO 11
<211> LENGTH: 19
```

```
<212> TYPE: PRT
<213> ORGANISM: Rousettus aegyptiacus

<400> SEQUENCE: 11

Lys Tyr Ser Asn Val Val Phe Leu Glu Val Asp Val Asp Asp Cys Gln
1               5                   10                  15

Asp Val Ala

<210> SEQ ID NO 12
<211> LENGTH: 19
<212> TYPE: PRT
<213> ORGANISM: Galeopterus Variegatus

<400> SEQUENCE: 12

Lys Tyr Ser Asn Val Val Phe Leu Glu Val Asp Val Asp Asp Cys Gln
1               5                   10                  15

Asp Val Ala

<210> SEQ ID NO 13
<211> LENGTH: 19
<212> TYPE: PRT
<213> ORGANISM: Vicugna Pacos

<400> SEQUENCE: 13

Lys Tyr Ser Asn Val Val Phe Leu Glu Val Asp Val Asp Asp Cys Gln
1               5                   10                  15

Asp Val Ala

<210> SEQ ID NO 14
<211> LENGTH: 19
<212> TYPE: PRT
<213> ORGANISM: Odobenus Rosmarus Divergens

<400> SEQUENCE: 14

Lys Tyr Ser Asn Val Val Phe Leu Glu Val Asp Val Asp Asp Cys Gln
1               5                   10                  15

Asp Val Ala

<210> SEQ ID NO 15
<211> LENGTH: 19
<212> TYPE: PRT
<213> ORGANISM: Acinonyx jubatus

<400> SEQUENCE: 15

Lys Tyr Ser Asn Val Val Phe Leu Glu Val Asp Val Asp Asp Cys Gln
1               5                   10                  15

Asp Val Ala

<210> SEQ ID NO 16
<211> LENGTH: 19
<212> TYPE: PRT
<213> ORGANISM: Mustela Putorius Furo

<400> SEQUENCE: 16

Lys Tyr Ser Asn Val Val Phe Leu Glu Val Asp Val Asp Asp Cys Gln
1               5                   10                  15

Asp Val Ala

<210> SEQ ID NO 17
<211> LENGTH: 19
<212> TYPE: PRT
```

<213> ORGANISM: Balaenoptera Acutorostrata Sca

<400> SEQUENCE: 17

Lys Tyr Ser Asn Val Val Phe Leu Glu Val Asp Val Asp Asp Cys Gln
1               5                   10                  15

Asp Val Ala

<210> SEQ ID NO 18
<211> LENGTH: 19
<212> TYPE: PRT
<213> ORGANISM: Sus scrofa

<400> SEQUENCE: 18

Lys Tyr Ser Asn Val Val Phe Leu Glu Val Asp Val Asp Asp Cys Gln
1               5                   10                  15

Asp Val Ala

<210> SEQ ID NO 19
<211> LENGTH: 19
<212> TYPE: PRT
<213> ORGANISM: Macaca mulatta

<400> SEQUENCE: 19

Lys Tyr Ser Asn Val Val Phe Leu Glu Val Asp Val Asp Asp Cys Gln
1               5                   10                  15

Asp Val Ala

<210> SEQ ID NO 20
<211> LENGTH: 19
<212> TYPE: PRT
<213> ORGANISM: Colobus angolensis

<400> SEQUENCE: 20

Lys Tyr Ser Asn Val Val Phe Leu Glu Val Asp Val Asp Asp Cys Gln
1               5                   10                  15

Asp Val Ala

<210> SEQ ID NO 21
<211> LENGTH: 19
<212> TYPE: PRT
<213> ORGANISM: Ceratotherium simum

<400> SEQUENCE: 21

Lys Tyr Ser Asn Val Val Phe Leu Glu Val Asp Val Asp Asp Cys Gln
1               5                   10                  15

Asp Val Ala

<210> SEQ ID NO 22
<211> LENGTH: 19
<212> TYPE: PRT
<213> ORGANISM: Callithrix jacchus

<400> SEQUENCE: 22

Lys Tyr Ser Asn Val Val Phe Leu Glu Val Asp Val Asp Asp Cys Gln
1               5                   10                  15

Asp Val Ala

<210> SEQ ID NO 23
<211> LENGTH: 19
<212> TYPE: PRT
<213> ORGANISM: Propithecus sp.

<400> SEQUENCE: 23

Lys Tyr Ser Asn Val Val Phe Leu Glu Val Asp Val Asp Asp Cys Gln
1               5                   10                  15

Asp Val Ala

<210> SEQ ID NO 24
<211> LENGTH: 19
<212> TYPE: PRT
<213> ORGANISM: Camelus sp.

<400> SEQUENCE: 24

Lys Tyr Ser Asn Val Val Phe Leu Glu Val Asp Val Asp Asp Cys Gln
1               5                   10                  15

Asp Val Ala

<210> SEQ ID NO 25
<211> LENGTH: 19
<212> TYPE: PRT
<213> ORGANISM: Manis javanica

<400> SEQUENCE: 25

Lys Tyr Ser Asn Val Val Phe Leu Glu Val Asp Val Asp Asp Cys Gln
1               5                   10                  15

Asp Val Ala

<210> SEQ ID NO 26
<211> LENGTH: 19
<212> TYPE: PRT
<213> ORGANISM: Ursus sp.

<400> SEQUENCE: 26

Lys Tyr Ser Asn Val Val Phe Leu Glu Val Asp Val Asp Asp Cys Gln
1               5                   10                  15

Asp Val Ala

<210> SEQ ID NO 27
<211> LENGTH: 19
<212> TYPE: PRT
<213> ORGANISM: Miniopterus Natalensis

<400> SEQUENCE: 27

Lys Tyr Ser Asn Val Val Phe Leu Glu Val Asp Val Asp Asp Cys Gln
1               5                   10                  15

Asp Val Ala

<210> SEQ ID NO 28
<211> LENGTH: 19
<212> TYPE: PRT
<213> ORGANISM: Cavia porcellus

<400> SEQUENCE: 28

Lys Tyr Ser Asn Val Val Phe Leu Glu Val Asp Val Asp Asp Cys Gln
1               5                   10                  15

Asp Val Ala

<210> SEQ ID NO 29
<211> LENGTH: 19
<212> TYPE: PRT
<213> ORGANISM: Aotus nancymaae

```
<400> SEQUENCE: 29

Lys Tyr Ser Asn Val Val Phe Leu Glu Val Asp Val Asp Asp Cys Gln
1               5                   10                  15

Asp Val Ala

<210> SEQ ID NO 30
<211> LENGTH: 19
<212> TYPE: PRT
<213> ORGANISM: Tursiops truncatus

<400> SEQUENCE: 30

Lys Tyr Ser Asn Val Val Phe Leu Glu Val Asp Val Asp Asp Cys Gln
1               5                   10                  15

Asp Val Ala

<210> SEQ ID NO 31
<211> LENGTH: 19
<212> TYPE: PRT
<213> ORGANISM: Ailuropoda melanoleuca

<400> SEQUENCE: 31

Lys Tyr Ser Asn Val Val Phe Leu Glu Val Asp Val Asp Asp Cys Gln
1               5                   10                  15

Asp Val Ala

<210> SEQ ID NO 32
<211> LENGTH: 19
<212> TYPE: PRT
<213> ORGANISM: Equus caballus

<400> SEQUENCE: 32

Lys Tyr Ser Asn Val Val Phe Leu Glu Val Asp Val Asp Asp Cys Gln
1               5                   10                  15

Asp Val Ala

<210> SEQ ID NO 33
<211> LENGTH: 19
<212> TYPE: PRT
<213> ORGANISM: Bos taurus

<400> SEQUENCE: 33

Lys Tyr Ser Asn Val Val Phe Leu Glu Val Asp Val Asp Asp Cys Gln
1               5                   10                  15

Asp Val Ala

<210> SEQ ID NO 34
<211> LENGTH: 19
<212> TYPE: PRT
<213> ORGANISM: Acinetobacter sp.

<400> SEQUENCE: 34

Lys Tyr Ser Asn Val Ile Phe Leu Glu Val Asp Val Asp Asp Cys Gln
1               5                   10                  15

Asp Val Ala

<210> SEQ ID NO 35
<211> LENGTH: 19
<212> TYPE: PRT
<213> ORGANISM: Homo sapiens

<400> SEQUENCE: 35
```

Lys Tyr Ser Asn Val Ile Phe Leu Glu Val Asp Val Asp Asp Cys Gln
1               5                   10                  15

Asp Val Ala

<210> SEQ ID NO 36
<211> LENGTH: 19
<212> TYPE: PRT
<213> ORGANISM: Nomascus Leucogenys

<400> SEQUENCE: 36

Lys Tyr Ser Asn Val Ile Phe Leu Glu Val Asp Val Asp Asp Cys Gln
1               5                   10                  15

Asp Val Ala

<210> SEQ ID NO 37
<211> LENGTH: 19
<212> TYPE: PRT
<213> ORGANISM: Octodon degus

<400> SEQUENCE: 37

Lys Tyr Ser Asn Val Leu Phe Leu Glu Val Asp Val Asp Asp Cys Gln
1               5                   10                  15

Asp Val Ala

<210> SEQ ID NO 38
<211> LENGTH: 19
<212> TYPE: PRT
<213> ORGANISM: Ictidomys Tridecemlineatus

<400> SEQUENCE: 38

Lys Tyr Ser Asn Val Leu Phe Leu Glu Val Asp Val Asp Asp Cys Gln
1               5                   10                  15

Asp Val Ala

<210> SEQ ID NO 39
<211> LENGTH: 19
<212> TYPE: PRT
<213> ORGANISM: Marmota marmota

<400> SEQUENCE: 39

Lys Tyr Ser Asn Val Leu Phe Leu Glu Val Asp Val Asp Asp Cys Gln
1               5                   10                  15

Asp Val Ala

<210> SEQ ID NO 40
<211> LENGTH: 19
<212> TYPE: PRT
<213> ORGANISM: Chinchilla laniger

<400> SEQUENCE: 40

Lys Tyr Ser Asn Val Leu Phe Leu Glu Val Asp Val Asp Asp Cys Gln
1               5                   10                  15

Asp Val Ala

<210> SEQ ID NO 41
<211> LENGTH: 19
<212> TYPE: PRT
<213> ORGANISM: Eptesicus fuscus

<400> SEQUENCE: 41

-continued

```
Lys Tyr Ser Asn Val Leu Phe Leu Glu Val Asp Val Asp Asp Cys Gln
1               5                   10                  15

Asp Val Ala
```